United States Patent
Koska

(10) Patent No.: US 11,382,833 B2
(45) Date of Patent: Jul. 12, 2022

(54) SYSTEMS AND METHODS FOR FLUID DELIVERY

(71) Applicant: Koska Family Limited, East Sussex (GB)

(72) Inventor: Marc Andrew Koska, East Sussex (GB)

(73) Assignee: KOSKA FAMILY LIMITED, East Sussex (GB)

(*) Notice: Subject to any disclaimer, the term of this patent is extended or adjusted under 35 U.S.C. 154(b) by 726 days.

(21) Appl. No.: 16/169,983

(22) Filed: Oct. 24, 2018

(65) Prior Publication Data
US 2019/0060168 A1 Feb. 28, 2019

Related U.S. Application Data

(63) Continuation-in-part of application No. PCT/IB2017/000549, filed on Apr. 25, 2017.
(Continued)

(51) Int. Cl.
*A61J 1/20* (2006.01)
*A61M 5/34* (2006.01)
(Continued)

(52) U.S. Cl.
CPC .......... *A61J 1/201* (2015.05); *A61J 1/067* (2013.01); *A61J 1/2096* (2013.01);
(Continued)

(58) Field of Classification Search
CPC .......... A61J 1/201; A61J 1/067; A61J 1/2096; A61J 1/18; A61M 5/2425; A61M 5/30;
(Continued)

(56) References Cited

U.S. PATENT DOCUMENTS

| 2,667,165 A | 1/1954 | Smith |
| 2,717,598 A | 9/1955 | Krasno |

(Continued)

FOREIGN PATENT DOCUMENTS

| AU | 2337470 | 6/1972 |
| CN | 1196023 A | 10/1998 |

(Continued)

OTHER PUBLICATIONS

International Search Report for PCT/US18/61696 dated Mar. 7, 2019; 2 pps.
(Continued)

*Primary Examiner* — Theodore J Stigell
(74) *Attorney, Agent, or Firm* — RowanTree Law Group, PLLC; Carson C. K. Fincham

(57) ABSTRACT

The invention provides for a delivery system including a delivery assembly configured to allow delivery of a single dose of a therapeutic agent (e.g., vaccine, drug, medicament, etc.) from a Blow-Fill-Seal (BFS) vial to a patient. The delivery assembly generally includes a modular design consisting of separately constructed components cooperatively arranged and coupled to one another. The modular construction allows for rapid manufacturing reconfigurations of one or more components with minimal costs to create new delivery assembly configurations that meet specific needs (i.e., different modes of delivery depending on agent to be delivered, such as subcutaneous, intramuscular, intradermal, intravenous injection, spray, or droplet delivery). The delivery assembly is generally configured to be filled on-site and in the field and is further capable of delivery of the agent in a controlled manner and without requiring specialized skill in administering delivery of such agent.

5 Claims, 23 Drawing Sheets

Related U.S. Application Data

(60) Provisional application No. 62/474,096, filed on Mar. 21, 2017, provisional application No. 62/326,977, filed on Apr. 25, 2016.

(51) Int. Cl.
  *A61M 5/24* (2006.01)
  *A61J 1/06* (2006.01)
  *A61M 5/28* (2006.01)
  *A61M 5/32* (2006.01)
  A61M 5/30 (2006.01)
  A61M 5/31 (2006.01)
  B29C 49/04 (2006.01)
  A61M 5/00 (2006.01)
  A61J 1/18 (2006.01)
  A61M 5/162 (2006.01)

(52) U.S. Cl.
  CPC .......... *A61M 5/2425* (2013.01); *A61M 5/343* (2013.01); *A61M 5/348* (2013.01); *A61J 1/18* (2013.01); *A61M 5/162* (2013.01); *A61M 5/282* (2013.01); *A61M 5/30* (2013.01); *A61M 5/3202* (2013.01); *A61M 2005/005* (2013.01); *A61M 2005/3128* (2013.01); *A61M 2205/12* (2013.01); *A61M 2205/3334* (2013.01); *B29C 49/04* (2013.01)

(58) Field of Classification Search
  CPC ...... A61M 5/343; A61M 5/348; A61M 5/162; A61M 5/282; A61M 5/3202; A61M 2005/005; A61M 2005/3128; A61M 2205/12; A61M 2205/3334; A61M 5/31531; B29C 49/04
  See application file for complete search history.

(56) References Cited

U.S. PATENT DOCUMENTS

| | | | |
|---|---|---|---|
| 3,073,307 A * | 1/1963 | Stevens | A61M 5/343 604/192 |
| 3,192,925 A | 7/1965 | Cunningham | |
| 3,640,388 A | 2/1972 | Ferrari | |
| 4,022,206 A | 5/1977 | Hilleman | |
| 4,643,309 A | 2/1987 | Evers | |
| 4,671,763 A | 6/1987 | Weiler | |
| 4,883,473 A | 11/1989 | Thomas | |
| 4,955,871 A | 9/1990 | Thomas | |
| 4,966,581 A | 10/1990 | Landau | |
| 5,135,514 A | 8/1992 | Kimber | |
| 5,139,489 A | 8/1992 | Hollister | |
| 5,217,480 A | 6/1993 | Haber | |
| 5,222,948 A | 6/1993 | Glenn et al. | |
| 5,261,881 A | 11/1993 | Riner | |
| 5,409,125 A | 4/1995 | Kimber | |
| 5,509,906 A | 4/1996 | Poynter | |
| 5,533,505 A | 7/1996 | Kallstrand | |
| 5,624,407 A | 4/1997 | Claro | |
| 5,636,640 A | 6/1997 | Staehlin | |
| D425,617 S | 5/2000 | Snedden | |
| 6,120,478 A | 9/2000 | Moore | |
| 6,200,296 B1 | 3/2001 | Dibiasi et al. | |
| 6,231,559 B1 | 5/2001 | Loretti | |
| D447,560 S | 9/2001 | Hellberg | |
| 6,379,342 B1 | 4/2002 | Levinson | |
| 6,383,166 B1 | 5/2002 | Farris | |
| D458,366 S | 6/2002 | Hellberg | |
| D462,760 S | 9/2002 | Ahlgrim | |
| 6,860,405 B1 | 3/2005 | Poynter | |
| 7,028,862 B2 | 4/2006 | Poynter | |
| 7,100,600 B2 | 9/2006 | Loeffler | |
| 7,487,894 B2 | 2/2009 | Zahn | |
| 7,513,397 B2 | 4/2009 | Zahn | |
| 7,632,253 B2 | 12/2009 | Ooyauchi | |
| 7,883,660 B2 | 2/2011 | Matsuda et al. | |
| 7,892,211 B2 | 2/2011 | McCulloch | |
| 8,133,202 B2 | 3/2012 | Marsh | |
| 8,434,643 B2 | 5/2013 | Harris | |
| 8,464,918 B1 | 6/2013 | Harris | |
| 8,652,096 B2 | 2/2014 | Alvey | |
| 8,663,188 B2 * | 3/2014 | Genosar | A61J 1/1406 604/411 |
| 8,795,226 B2 | 8/2014 | Kuhn et al. | |
| 9,132,238 B2 | 9/2015 | Ferreri | |
| 9,242,051 B2 | 1/2016 | Jugl et al. | |
| 9,265,889 B2 | 2/2016 | Thornton | |
| D753,292 S | 4/2016 | Oates, II et al. | |
| 9,364,393 B1 | 6/2016 | Grabowski | |
| 9,526,839 B2 | 12/2016 | Chia | |
| D776,266 S | 1/2017 | Dombrowski | |
| 9,737,664 B2 | 8/2017 | Gardner | |
| 9,808,608 B2 | 11/2017 | Webb | |
| 9,820,913 B2 | 11/2017 | Genosar | |
| 10,064,785 B2 | 9/2018 | Spallek | |
| 10,117,994 B2 | 11/2018 | Holtwick et al. | |
| 10,118,000 B2 | 11/2018 | Schraga | |
| 10,149,939 B2 | 12/2018 | Giambattista et al. | |
| 10,207,053 B2 | 2/2019 | Groskoff et al. | |
| 10,278,896 B2 | 5/2019 | Brandenburger | |
| D859,647 S | 9/2019 | Chang | |
| 10,512,591 B2 | 12/2019 | Oshgan et al. | |
| 10,525,212 B2 | 1/2020 | Thornton | |
| 10,639,839 B2 | 5/2020 | Consolaro | |
| 10,821,053 B2 | 11/2020 | Rajagopal et al. | |
| 10,967,126 B2 | 4/2021 | Holtwick et al. | |
| 2003/0050602 A1 | 3/2003 | Pettis et al. | |
| 2003/0186456 A1 | 10/2003 | Stroup | |
| 2004/0118477 A1 | 6/2004 | Desmond | |
| 2007/0260188 A1 | 11/2007 | Kelly et al. | |
| 2008/0083691 A1 | 4/2008 | Poynter | |
| 2009/0025823 A1 | 1/2009 | Hansen | |
| 2009/0171311 A1 | 7/2009 | Genosar | |
| 2009/0216212 A1 | 8/2009 | Fangrow | |
| 2009/0230077 A1 | 9/2009 | Poynter | |
| 2011/0224640 A1 | 9/2011 | Kuhn et al. | |
| 2011/0135720 A1 | 12/2011 | Marshall | |
| 2012/0083744 A1 | 4/2012 | Finke et al. | |
| 2012/0179109 A1 | 7/2012 | Takemoto et al. | |
| 2013/0110053 A1 | 5/2013 | Yoshino et al. | |
| 2013/0345672 A1 | 12/2013 | Ferreri | |
| 2013/0345673 A1 | 12/2013 | Ferreri | |
| 2014/0008366 A1 | 1/2014 | Genosar | |
| 2014/0046270 A1 | 2/2014 | Thornton | |
| 2014/0054295 A1 | 2/2014 | Holtwick et al. | |
| 2014/0224815 A1 | 8/2014 | Gallem et al. | |
| 2014/0323975 A1 | 10/2014 | Thornton et al. | |
| 2015/0136622 A1 | 5/2015 | Genosar | |
| 2016/0074586 A1 | 3/2016 | Mernoe et al. | |
| 2016/0144130 A1 | 5/2016 | Thornton | |
| 2016/0175544 A1 | 6/2016 | Koska | |
| 2018/0072480 A1 | 3/2018 | Genosar | |
| 2018/0193565 A1 | 7/2018 | Koska | |
| 2018/0193571 A1 | 7/2018 | Koska | |
| 2018/0193572 A1 | 7/2018 | Koska | |
| 2018/0235840 A1 | 8/2018 | Genosar | |
| 2019/0046402 A1 | 2/2019 | Besbrosses et al. | |
| 2019/0060168 A1 | 2/2019 | Koska | |
| 2019/0060573 A1 | 2/2019 | Consolaro et al. | |
| 2019/0224424 A1 | 7/2019 | Helmer et al. | |
| 2020/0100985 A1 | 4/2020 | Auerbach | |
| 2020/0129698 A1 | 4/2020 | Chowdhury | |
| 2020/0164563 A1 | 5/2020 | Spallek | |
| 2021/0030965 A1 | 2/2021 | Koska | |
| 2021/0128835 A1 | 5/2021 | Koska | |

FOREIGN PATENT DOCUMENTS

| | | |
|---|---|---|
| EP | 0310227 | 4/1989 |
| EP | 0388360 | 9/1990 |
| EP | 0903180 | 3/1999 |
| EP | 1726285 | 11/2006 |
| EP | 2665502 | 7/2012 |

(56) References Cited

FOREIGN PATENT DOCUMENTS

| | | |
|---|---|---|
| EP | 2554201 | 6/2013 |
| EP | 2554207 | 6/2013 |
| EP | 2571553 | 6/2014 |
| EP | 3173113 | 5/2017 |
| EP | 3518860 | 4/2018 |
| EP | 2919834 | 5/2018 |
| GB | 2490111 | 10/2012 |
| GB | 2495741 | 4/2013 |
| IN | 201741030340 | 1/2019 |
| JP | 2015109883 | 6/2015 |
| KR | 200345715 | 3/2004 |
| KR | 100615527 | 8/2006 |
| RU | 2643432 | 1/2018 |
| WO | WO 1989/007462 | 8/1989 |
| WO | WO 1993/017728 | 9/1993 |
| WO | WO1997010156 | 3/1997 |
| WO | WO1998025660 | 6/1998 |
| WO | WO 2001/043799 | 6/2001 |
| WO | WO2001043799 | 6/2001 |
| WO | WO 2011/008190 | 1/2011 |
| WO | WO2011026050 | 3/2011 |
| WO | WO 2011/075798 | 6/2011 |
| WO | WO2012011115 | 1/2012 |
| WO | WO2012064761 | 5/2012 |
| WO | WO2012099898 | 7/2012 |
| WO | WO2012148043 | 11/2012 |
| WO | WO2013114357 | 8/2013 |
| WO | WO20140035935 | 3/2014 |
| WO | WO2015045740 | 2/2015 |
| WO | WO2015036536 | 3/2015 |
| WO | WO 2015/074087 | 5/2015 |
| WO | 2016097872 | 6/2016 |
| WO | 2017001918 | 1/2017 |
| WO | 2017001919 | 1/2017 |
| WO | 2017001921 | 1/2017 |
| WO | 2017001922 | 1/2017 |
| WO | 2017001923 | 1/2017 |
| WO | WO2017001925 | 1/2017 |
| WO | WO 2017/001925 | 5/2017 |
| WO | WO2017125859 | 7/2017 |
| WO | WO2017187262 | 11/2017 |
| WO | 2019099954 | 5/2019 |
| WO | WO 2019/246435 | 12/2019 |
| WO | 2021207040 | 10/2021 |
| WO | 2021226564 | 11/2021 |
| WO | 2022026275 | 2/2022 |
| WO | 2022053948 | 3/2022 |
| WO | 2022091003 | 5/2022 |

OTHER PUBLICATIONS

Written Opinion or PCT/US18/61696 dated Mar. 7, 2019; 3 pps.
Office Action for U.S. Appl. No. 15/741,009 dated Oct. 2, 2019; 6 pps.
Office Action for U.S. Appl. No. 15/741,011 dated Oct. 2, 2019; 8pps.
Notice of Grant for 16774977.9 dated Mar. 12, 2020; 2 pps.
Syrette "https://en.wikipedia.org/wiki/Syrette" download date: Apr. 23, 2020; 2 pps.
Office Action for U.S. Appl. No. 15/741,012 dated Oct. 2, 2019; 7pps.
International Search Report for PCT/US2019/038302 dated Dec. 19, 2019; 2 pps.
Written Opinion or PCT/US2019/038302 dated Dec. 19, 2019; 4pps.
Written Opinion for WO 2016097872 dated May 6, 2016; 2 pps.
International Search Report for WO 2016097872 dated May 9, 1 pps.
Written Opinion for PCT/IB216/001042 dated Dec. 20, 2016; 6 pps.
Written Opinion for PCT/IB2016/001026 dated Nov. 7, 2016; 5 pps.
International Search Report or PCT/IB2016/001026 dated Nov. 8, 2016; 3 pps.
Written Opinion for PCT/IB2016/001027 dated Nov. 2, 2016; 5 pps.
International Search Report for PCT/IB2016/001027 dated Jan. 5, 2017; 2 pps.
Written Opinion for PCT/IB2016/001033 dated Dec. 7, 2016; 6 pps.
Written Opinion for PCT/IB2016/001050 dated Nov. 14, 2016; 5 pps.
International Search Report for PCT/IB2016/001050 dated Nov. 15, 2016; 2 pps.
Written Opinion for PCT/IIB2016/001034 dated Dec. 9, 2016; 6 pps.
Examination Report for PCT/IB2015/002531 dated May 28, 2020; 5 pps.
International Preliminary Report on Patentability for PCT/US18/61696 dated May 28, 2020; 4pps.
Written Opinion for WO2017/187262 dated Sep. 1, 2017; 7 pps.
International Search Report for WO2017/187262 dated Nov. 2, 2017; 3 pps.
International Search Report for Application PCT/US21/31452 dated Sep. 1, 2021; 2 pps.
Written Opinion for Application PCT/US21/31452 dated Sep. 1, 2021; 15 pps.
Office Action for Australian Application 2017256152 dated Jul. 29, 2021; 6 pps.
Office Action for Chinese Application 201780025582.0 dated Oct. 30, 2020; 2 pps.
Office Action for Indian Application 201827038286 dated Aug. 6, 2021; 6 pps.
Search Report for European Application 18877931.8 dated Oct. 19, 2021; 10 pps.
Office Action for Chinese Application 201680050853.3 dated Nov. 27, 2020; 3 pps.
Office Action for Chinese Application 201680050853.3 dated Mar. 18, 2020; 3 pps.
Office Action for Indian Application 201827038286 dated Jul. 2, 2021; 8 pps.
International Search Report for Application PCT/US21/042671 dated Nov. 5, 2021; 2 pps.
Written Opinion for Application PCT/US21/042671 dated Nov. 5, 2021; 9 pps.
International Search Report for Application PCT/IB2021/059993 dated Nov. 22, 2021; 8 pps.
Written Opinion for Application PCT/IB2021/059993 dated Nov. 22, 2021; 10 pps.
International Search Report for Application PCT/US2021/025683 dated Jul. 8, 2021; 2 pps.
Written Opinion for Application PCT/US2021/025683 dated Jul. 8, 2021; 4 pps.
International Search Report for Application PCT/US21/61991 dated Feb. 16, 2022; 2 pps.
Written Opinion for Application PCT/US21/61991 dated Feb. 16, 2022; 9 pps.
Office Action for Mexican Application MX/a/2018/000257 dated Mar. 2, 2022; 5 pps.
Office Action for Chinese Application 201880087016.7 dated Feb. 24, 2022; 7 pps.
Written Opinion for PCT/US21/064155 dated Mar. 21, 2022; 3 pps.
International Search Report for Application PCT/US21/064155 dated Mar. 21, 2022; 2 pps.
International Search Report for Application PCT/IB2021/058168 dated Nov. 22, 2021; 6 pps.
Written Opinion for PCT/IB2021/058168 dated Nov. 22, 2021; 9 pps.
International Search Report for Application PCT/IB2016/001034 dated Dec. 13, 2016; 3 pps.
International Search Report for Application PCT/IB2016/001033 dated Dec. 9, 2016; 4 pps.
International Search Report for Application PCT/IB2016/001042 dated Dec. 22, 2016; 3 pps.
Supplemental European Search Report for European Application No. 19823345.4 dated Feb. 7, 2022; 6 pps.
Office Action for Australian Application 2017256152 dated Nov. 12, 2021; 4 pps.

(56) References Cited

OTHER PUBLICATIONS

Notice of Acceptance for Australian Application 2017256152 dated Apr. 11, 2022; 3 pps.
Allowance Notification for Chinese Application 201780025582.0 dated Jun. 21, 2021; 1 pp.
Office Action for Korean Patent Application No. 10-2018-7030866 dated Sep. 24, 2021; 17 pps.
Office Action for Korean Patent Application No. 10-2018-7030866 dated Mar. 30, 2022; 4 pps.
Office Action for Chinese Application 201880087016.7 dated Sep. 14, 2021; 3 pps.
Search Report for European Application 18877931.8 dated Jul. 7, 2021; 9 pps.
Office Action (Non-final) for U.S. Appl. No. 14/575,635 dated Mar. 23, 2017; 44 pps.
Office Action (Final) for U.S. Appl. No. 14/575,635 dated Dec. 14, 2017; 44 pps.
Office Action (Non-final) for U.S. Appl. No. 14/575,635 dated Oct. 9, 2018; 39 pps.
Office Action (Non-final) for U.S. Appl. No. 15/741,009 dated Oct. 2, 2019; 6 pps.
Office Action (Non-final) for U.S. Appl. No. 15/741,011 dated Oct. 2, 2019; 8 pps.
Allowance Notification for Chinese Application 201680050853.3 dated Jun. 8, 2021; 1 pp.
Office Action (Notice of Allowance and Fees Due (PTOL-85)) dated Jul. 10, 2020 for U.S. Appl. No. 15/741,012 (pp. 1-6).

* cited by examiner

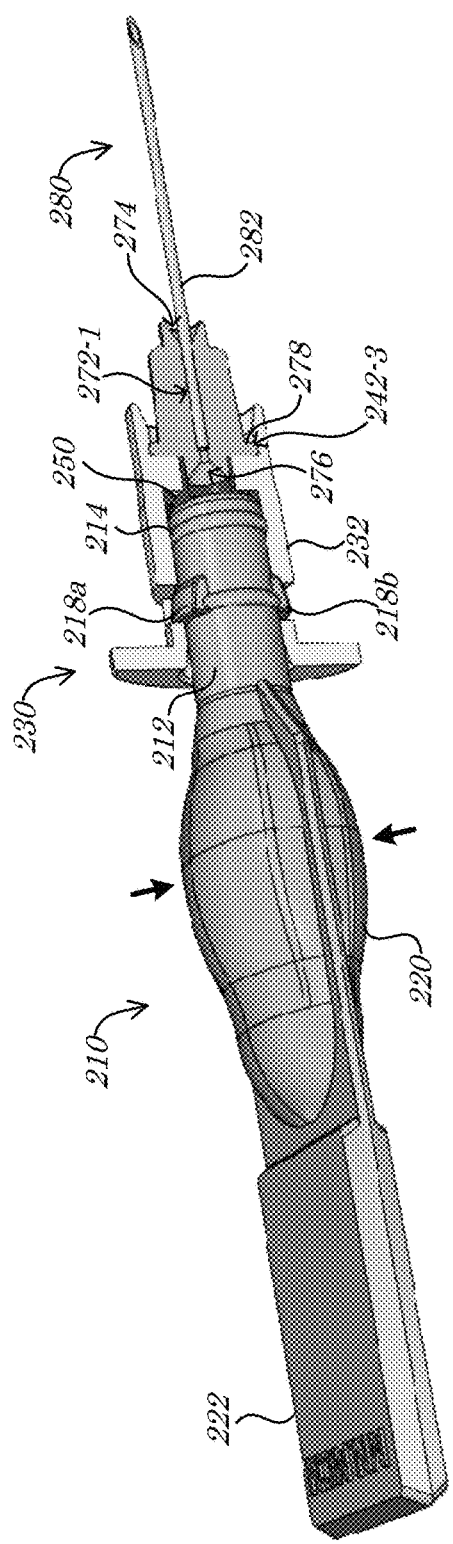
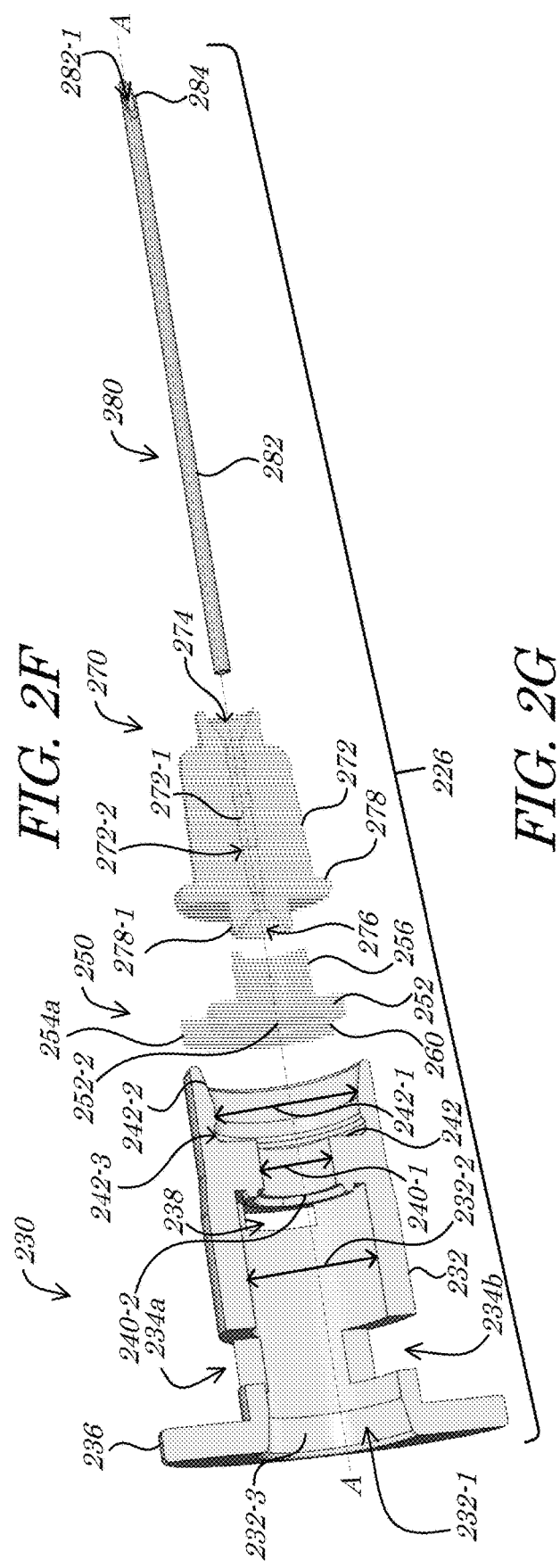
FIG. 2F
FIG. 2G

SYSTEMS AND METHODS FOR FLUID DELIVERY

CROSS-REFERENCE TO RELATED APPLICATIONS

This application claims the benefit and priority to, and is a Continuation-in-Part (CiP) of, International Patent Application PCT/IB2017/000549 filed on Apr. 25, 2017 and titled "MEDICAL DELIVERY SYSTEM", which itself claims benefit and priority to U.S. Provisional Application Ser. No. 62/326,977 filed on Apr. 25, 2016 and to U.S. Provisional Application Ser. No. 62/474,096 filed on Mar. 21, 2017, the contents of each of such previous applications of which is hereby incorporated by reference herein in the entirety.

FIELD OF THE INVENTION

Embodiments of the present invention generally relate to delivery devices for delivering substances, such as medicaments, and, more particularly, to a delivery system including a modular delivery assembly configured to allow delivery of a single dose of a therapeutic agent from a Blow-Fill-Seal (BFS) vial to a patient.

BACKGROUND

Every year, millions of people become infected and die from a variety of diseases, some of which are vaccine-preventable. Although vaccination has led to a dramatic decline in the number of cases of several infectious diseases, some of these diseases remain quite common. In many instances, large populations of the world, particularly in developing countries, suffer from the spread of vaccine-preventable diseases due to ineffective immunization programs, either because of poor implementation, lack of affordable vaccines, or inadequate devices for administering vaccines, or combinations thereof.

Some implementations of immunization programs generally include administration of vaccines via a typical reusable syringe. However, in many situations, particularly in developing countries, the administration of vaccines occur outside of a hospital and may be provided by a non-professional, such that injections are given to patients without carefully controlling access to syringes. The use of reusable syringes under those circumstances increases the risk of infection and spread of blood-borne diseases, particularly when syringes, which have been previously used and are no longer sterile, are used to administer subsequent injections. For example, the World Health Organization (WHO) estimates that blood-borne diseases, such as Hepatitis and human immunodeficiency virus (HIV), are being transmitted due to reuse of such syringes, resulting the death of more than one million people each year.

SUMMARY

Embodiments of the present invention provide a delivery system that overcomes the drawbacks of current delivery devices and methods. In particular, the delivery system according to some embodiments includes a modular delivery assembly configured to be coupled to a source containing a fluid agent (e.g., vaccine, drug, medicament, etc.) and further facilitate delivery of a single dose of the fluid agent from the source to a patient. The delivery assembly may be configured to be filled on-site and in the field with a single dose of a fluid agent, while remaining sterile and preventing the potential for contamination during the filling process, or may be pre-filled (e.g., during manufacture). The delivery assembly may also or alternatively be capable of delivering a fluid agent in a controlled manner and without requiring specialized skill in administering delivery of such agent.

In particular, the modular delivery assembly in accordance with some embodiments may be configured to be coupled to a source containing a fluid agent, including, but not limited to, a Blow-Fill-Seal (BFS) vial. The delivery assembly may include a modular design consisting of separately constructed modular components cooperatively arranged and coupled to one another. The components of the delivery assembly may include, for example, a hub member configured to be securely coupled to the BFS vial, a one-way valve member positioned within the hub member and configured to limit fluid flow to an antegrade direction, and an insert positioned within the hub member and configured to receive and retain an administration member for receiving the fluid agent from the BFS vial and administering the fluid agent into a patient. The administration member may include, for example, a needle (for subcutaneous, intramuscular, intradermal, or intravenous injection of the fluid agent) or a nozzle (e.g., spray nozzle to facilitate dispersion of the fluid agent into a spray or a droplet nozzle for formation of droplets).

In some embodiments, the hub member may include a proximal end defining an inlet port and a distal end defining an outlet port and a channel extending entirely from the proximal end to the distal end, thereby providing a fluid pathway between inlet and outlet ports. The inlet port may include a specialty, non-standard (non-Luer-type connection) connection fitting configured to be coupled with a corresponding specialty, non-standard connection fitting of a BFS vial. For example, the inlet port may include recesses, depressions, or complete apertures of a particular shape or geometry which are shaped and/or sized to receive correspondingly shaped and/or sized protrusions, projections, or the like on the BFS vial. In some embodiments, the inlet port may include two opposing apertures on either side of the hub member. The BFS vial may generally include a flexible body having an interior volume sufficient to contain at least one dose of the fluid agent within. The BFS vial may generally include a neck extending from the body and terminating at a distal end defining an outlet for dispensing the fluid agent upon squeezing of the vial body. In some embodiments, the vial may include two (2) protrusions defined on opposing sides of the neck adjacent to the distal end and having a general shape corresponding to the apertures on the hub member. Upon a user inserting the distal end of the vial into the inlet port of the hub member, for example, the protrusions may be shaped so as to slide into engagement with the corresponding apertures but further shaped to prevent withdrawal of the BFS vial from the hub member, thereby effectively locking themselves within the apertures and effectively locking the BFS vial into engagement with the delivery assembly. By securing the vial to the hub member, a user need only apply force to (i.e., squeeze) the vial body to cause the fluid agent to flow from the vial, through the delivery assembly, and to the patient.

The specialty, non-standard connection fitting between the hub member and the BFS vial in some embodiments may allow for only approved sources (e.g., single-dose BFS vials) with a corresponding agent to be used with the modular delivery assembly described herein, thereby adding a layer of security. For example, the method of delivery is generally dependent on the type of fluid agent to be delivered. For example, some medicaments are best delivered intravenously while some vaccines are best delivered intradermally, and yet still, some fluid agents are administered via droplets or spray. Accordingly, the delivery assembly may be configured for delivery of a specific fluid agent and thus the connection fitting on the hub member may be designed so as to only accept and engage a corresponding connection fitting of a BFS vial containing that specific fluid agent. Accordingly, the specialty connection fitting design described herein may ensure that only the matching BFS vial (which contains the correct fluid agent for that specific delivery assembly) is able to be connected to the modular delivery assembly, thereby ensuring safety and reducing risk.

As previously described, the delivery assembly may include a one-way valve and/or an insert within the hub member. The one-way valve may be positioned, for example, within the within the channel of the hub member and/or may be configured to limit fluid flow to an antegrade direction from the inlet port towards the outlet port, thereby ensuring that fluid flows in a single direction when the vial body is squeezed for delivery. The insert may, in some embodiments, be positioned within the channel adjacent to the outlet end of the hub member. The insert may include a proximal end and an opposing distal end and a channel extending entirely through the insert from the proximal end to the distal end. The channel of the insert may be in coaxial alignment with the channel of the hub member, such that the fluid pathway extends entirely from the inlet port of the hub member, through the one-way valve, and through the channel of the insert towards the distal end of the insert. The administration member (e.g., needle, nozzle, etc.) may be received and retained within the channel of the insert, such that, upon delivery of the fluid agent from the BFS vial and through the fluid pathway of the delivery assembly, the fluid agent will flow out of the administration member, thereby allowing for delivery of the fluid agent to the patient.

In some embodiments, the delivery assembly may include a safety cover for covering the administration member to prevent contamination and further reduce the risk of needlestick injuries, and thus reduce the potential for spreading blood-borne diseases. The delivery assembly may generally be packaged and delivered in a fully assembled state, including the safety cover provided over the needle or nozzle. Accordingly, a user does not have to deal with an exposed needle or nozzle when first attaching a BFS vial to the delivery assembly. Rather, the user need only remove the safety cover once the BFS vial has been securely attached to the delivery assembly to thereby expose the needle or nozzle for fluid agent delivery. The user may then replace the cover once delivery is complete.

The modular construction of the delivery assembly allows for rapid manufacturing reconfigurations of one or more components with minimal costs to create new delivery assembly configurations that meet specific needs (i.e., different modes of delivery depending on agent to be delivered, such as subcutaneous, intramuscular, intradermal, intravenous injection, spray, or droplet delivery). For example, the hub member and the one-way valve may remain the same construction (dimensions and material), while the insert may be changed to account for different needle sizes and/or nozzle types, depending on the type of delivery and/or type of fluid agent to be delivered.

The delivery assembly itself may not be not prefilled. As such, the delivery assembly may not be required to be maintained at a certain temperature (e.g., two to eight degrees Celsius (2° C.-8° C.)) during shipment or storage, thus cutting down on the overall costs. Rather than maintaining the delivery assembly at a constant temperature, as is the case with current devices, only the source containing the fluid agent (e.g., single dose supply provided in a BFS vial) need by maintained at a constant temperature. Accordingly, a plurality of empty delivery assemblies may be shipped and stored, at a reduced cost, and then filled directly on-site and on an as-needed basis, such that only the single-dose BFS vials need be stored and maintained. Additionally, in the case that the delivery device is not prefilled, it may be sterilized at any point prior to being filled with the fluid agent, which further improves the bulk shipping and storage of such devices.

According to some embodiments, the delivery assembly may be configured to allow delivery of the agent to the patient in a relatively simple manner, without requiring specialized training for administering the agent. In particular, the delivery assembly may be designed such that a person administering the fluid agent (e.g., administrator), which could also include self-administration, need only position the device upon the administration site (e.g., shoulder, arm, chest, nose, ear, eye, etc.), and then fully compress the BFS vial body containing the dose of fluid agent, thereby delivering the correct predefined dosage to the patient. The delivery assembly may also or alternatively be configured such that, in the event that a needle is required (i.e., because the delivery method is an injection), needle penetration is limited to the correct length and orientation within the administration site. For example, in some embodiments, the needle may be positioned substantially perpendicular relative to a plane along which the distal end of the insert lies, such that the needle is configured to be inserted into a patient's skin at a substantially perpendicular angle and the distal end of the insert is configured to contact the patient's skin indicating adequate depth of penetrating for injection of the fluid agent. Accordingly, embodiments of the modular delivery assembly described herein may not require a trained, skilled healthcare profession for administration of vaccines or drugs. As such, the delivery assembly may be particularly useful in situations in which vaccines or drugs are being administered in non-healthcare related facilities (e.g., outside of clinics or hospitals) and given to large numbers of individuals over a short period of time by a non-professional.

BRIEF DESCRIPTION OF THE DRAWINGS

The figures depict embodiments for purposes of illustration only. One skilled in the art will readily recognize from the following description that alternative embodiments of the systems and methods illustrated herein may be employed without departing from the principles described herein, wherein:

FIG. 1A is a perspective view of BFS vial package according to some embodiments;

FIG. 1B is a perspective close-up view of a portion of a BFS vial package according to some embodiments FIG. 2A and FIG. 2B are right-side views of a fluid delivery system according to some embodiments;

FIG. 2C and FIG. 2D are right-side views of a portion of the fluid delivery system according to some embodiments;

FIG. 2E is an exploded right-side view of a hub assembly of the fluid delivery system according to some embodiments;

FIG. 2F is a right-side cross-sectional view of the fluid delivery system according to some embodiments;

Figure 8:
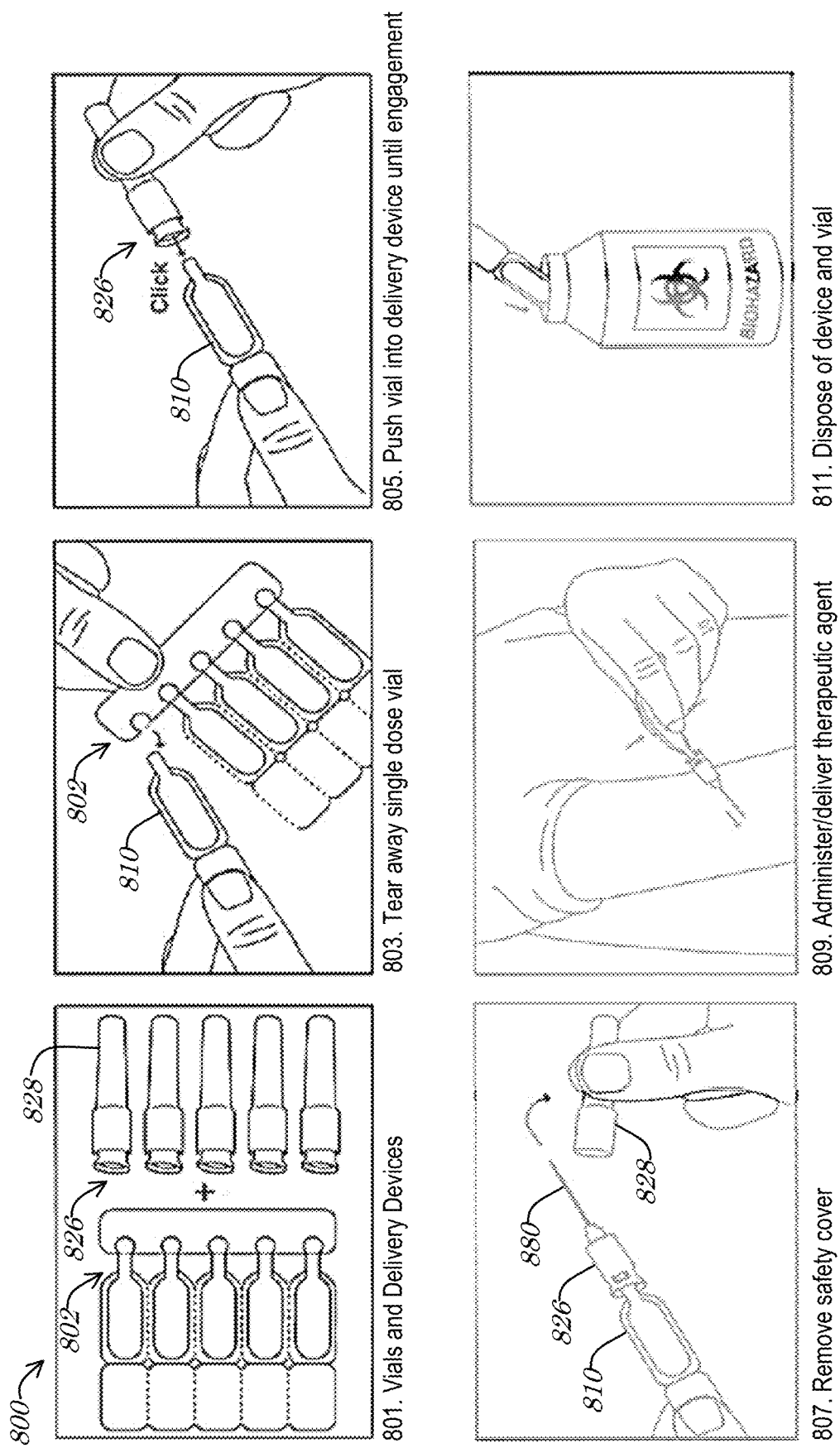
Figure 9:
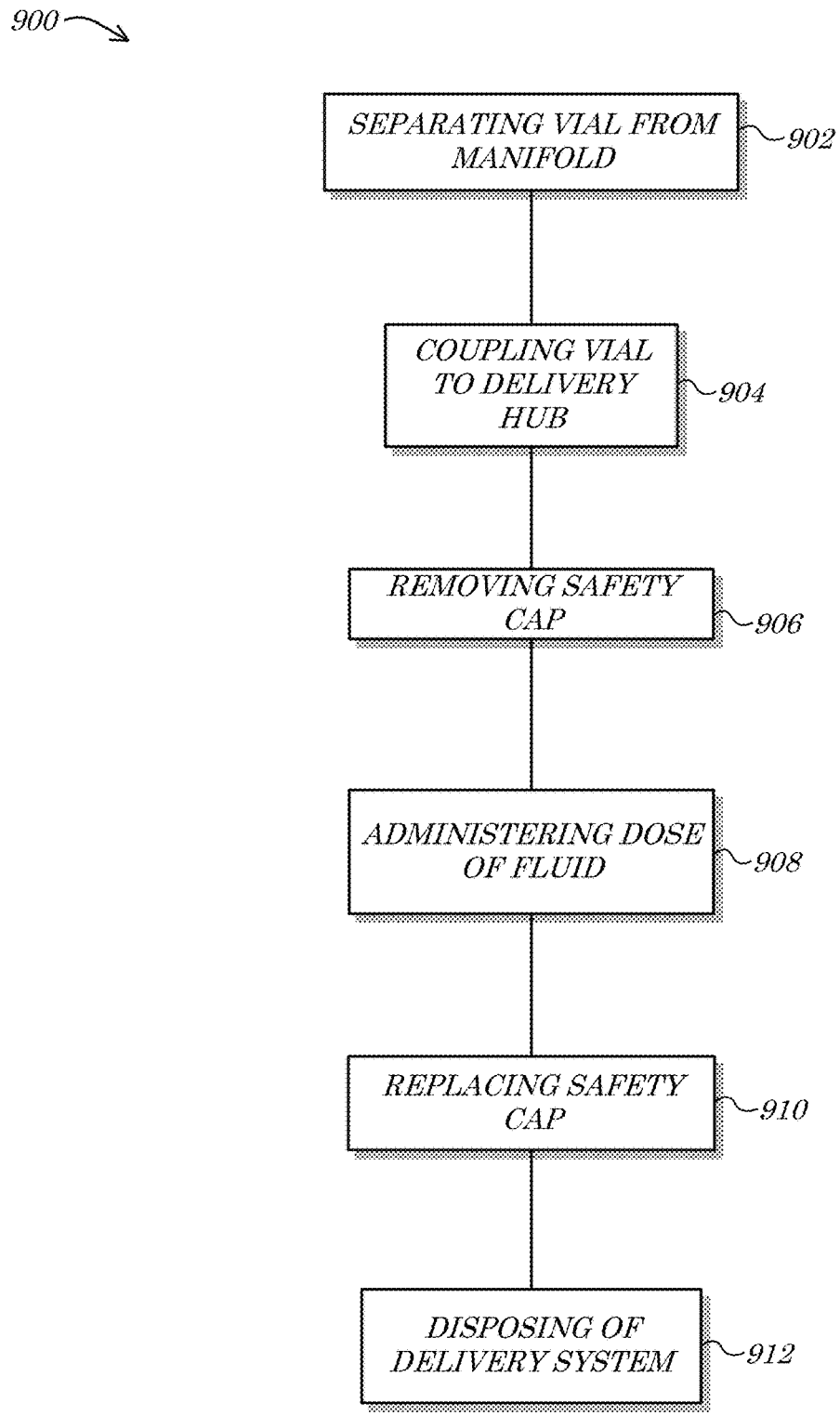

FIG. 3A, FIG. 3B, FIG. 3C, FIG. 3D, FIG. 3E, FIG. 3F, FIG. 3G, and FIG. 3H are right-front perspective, top, bottom, left, right, front, back, and front cross-sectional views of a modular hub according to some embodiments;

FIG. 4A, FIG. 4B, FIG. 4C, FIG. 4D, FIG. 4E, FIG. 4F, FIG. 4G, and FIG. 4H are right-front perspective, top, bottom, left, right, front, back, and front cross-sectional views of a modular valve according to some embodiments;

FIG. 5A, FIG. 5B, FIG. 5C, FIG. 5D, FIG. 5E, FIG. 5F, FIG. 5G, and FIG. 5H are right-front perspective, top, bottom, left, right, front, back, and front cross-sectional views of a modular insert according to some embodiments;

FIG. 6A, FIG. 6B, FIG. 6C, FIG. 6D, FIG. 6E, FIG. 6F, and FIG. 6G are right-front perspective, top, bottom, left, right, front, and views of a modular BFS vial according to some embodiments;

FIG. 7A, FIG. 7B, FIG. 7C, FIG. 7D, FIG. 7E, FIG. 7F, and FIG. 7G are right-front perspective, top, bottom, left, right, front, and views of a modular BFS vial according to some embodiments;

FIG. 8 is a perspective flow diagram of a method according to some embodiments;

FIG. 9 is a flow diagram of a method according to some embodiments; and

Figure 10:
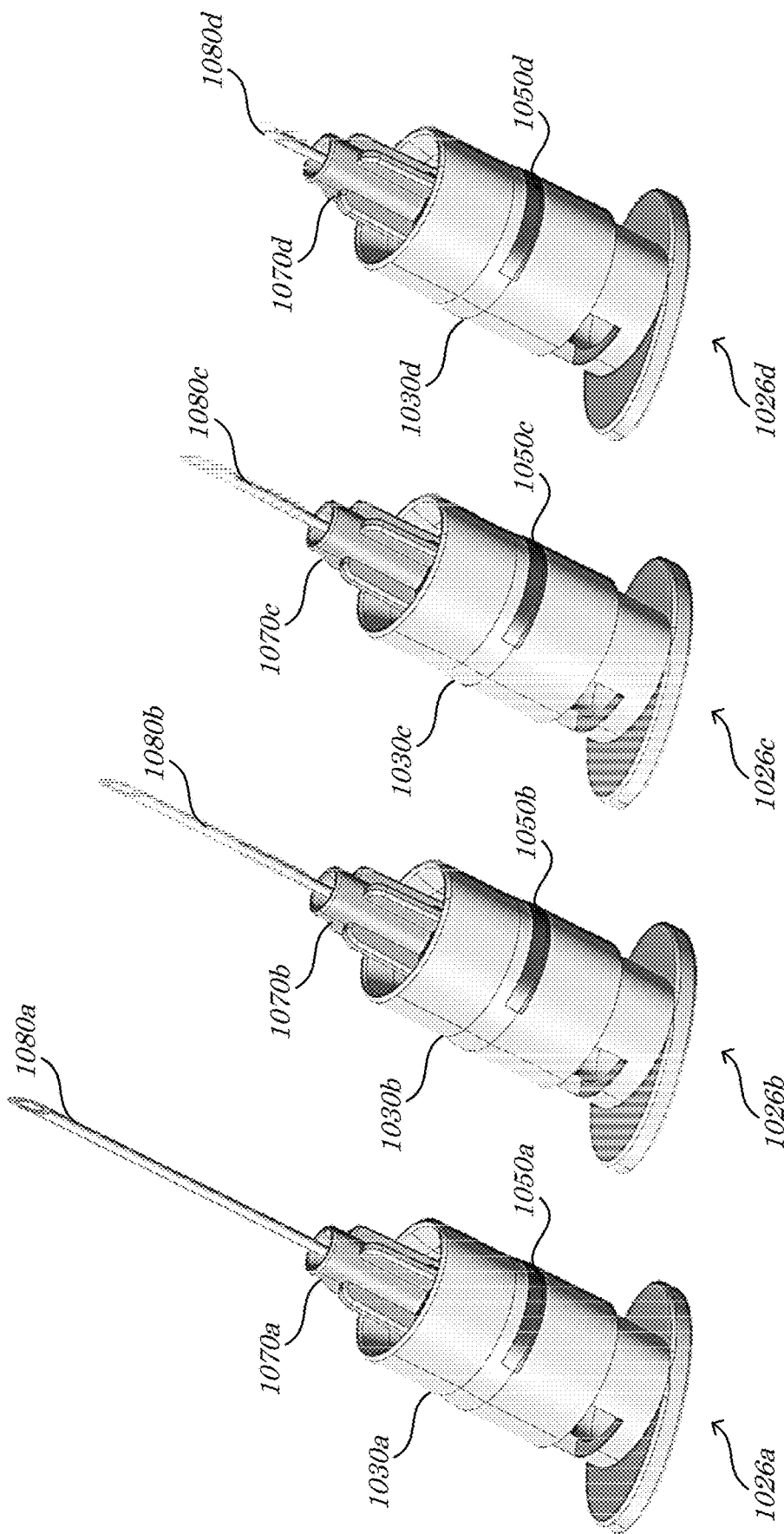

FIG. 10 is a perspective view of variations of hub assemblies according to some embodiments.

DETAILED DESCRIPTION

I. Introduction

Embodiments of the present invention provide a modular delivery system that overcomes the drawbacks of current delivery devices and methods. For example, the delivery system of some embodiments includes a modular delivery assembly configured to be coupled to a source containing a fluid agent (e.g., vaccine, drug, medicament, etc.) and further facilitate delivery of a single dose of the fluid agent from the source to a patient. The delivery assembly may be configured to be filled on-site and in the field with a single dose of a fluid agent, while remaining sterile and preventing the potential for contamination during the filling process. The delivery assembly may also or alternatively be capable of delivering the fluid agent in a controlled manner and without requiring specialized skill in administering delivery of such agent.

The delivery assembly in accordance with some embodiments may be configured to be coupled to a source containing the fluid agent, including, but not limited to, a BFS vial.

The delivery assembly may generally include a modular design consisting of separately constructed components cooperatively arranged and coupled to one another. The components of the delivery assembly may include, for example, a hub member configured to be securely coupled to the BFS vial, a one-way valve member positioned within the hub member and configured to limit fluid flow to an antegrade direction, and/or an insert positioned within the hub member and configured to receive and retain an administration member for receiving the fluid agent from the BFS vial and administering the fluid agent into a patient. The administration member may include, for example, a needle (for subcutaneous, intramuscular, intradermal, or intravenous injection of the fluid agent) or a nozzle (e.g., spray nozzle to facilitate dispersion of the fluid agent into a spray or a droplet nozzle for formation of droplets).

The modular construction of the delivery assembly may allow for rapid manufacturing reconfigurations of one or more components with minimal costs to create new delivery assembly configurations that meet specific needs (i.e., different modes of delivery depending on agent to be delivered, such as subcutaneous, intramuscular, intradermal, intravenous injection, spray, or droplet delivery). For example, the hub member and the one-way valve may remain the same construction (dimensions and material), while the insert may be changed to account for different needle sizes and/or nozzle types, depending on the type of delivery and/or type of fluid agent to be delivered.

The delivery assembly may generally be configured to allow delivery of the agent to the patient in a relatively simple manner, without requiring specialized training for administering the agent. In particular, the delivery assembly is designed such that a person administering the fluid agent (e.g., administrator), which could also include self-administration, need only position the device upon the administration site (e.g., shoulder, arm, chest, nose, ear, eye, etc.), and then fully compress the BFS vial body containing the dose of fluid agent, thereby delivering the correct predefined dosage to the patient.

The delivery assembly itself may not be prefilled. As such, the delivery assembly according to some embodiments may not require the maintenance of a certain temperature (e.g., two to eight degrees Celsius (2° C.-8° C.)) during shipment or storage, thus cutting down on the overall costs. Rather than maintaining the delivery assembly at a constant temperature, as is the case with current devices, only the source containing the fluid agent (e.g., single dose supply provided in a BFS vial) need by maintained at a constant temperature, for example. Accordingly, a plurality of empty delivery assemblies may be shipped and stored, at a reduced cost, and then filled directly on-site and on an as-needed basis, such that only the single-dose BFS vials need be stored and maintained. Additionally, in the case that the delivery device is not prefilled, it may be sterilized at any point prior to being filled with the fluid agent, which further improves the bulk shipping and storage of such devices.

II. Fluid Delivery Systems

Figure 1A:
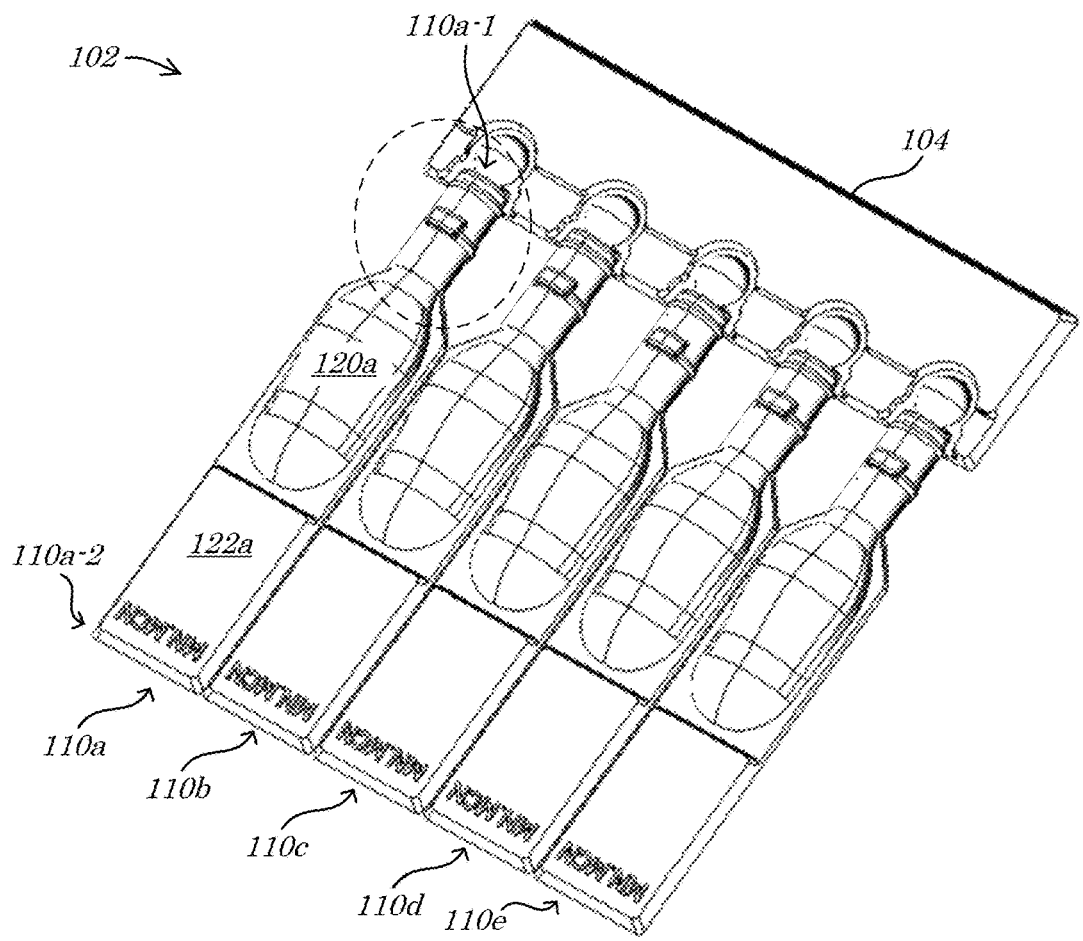
Figure 1B:
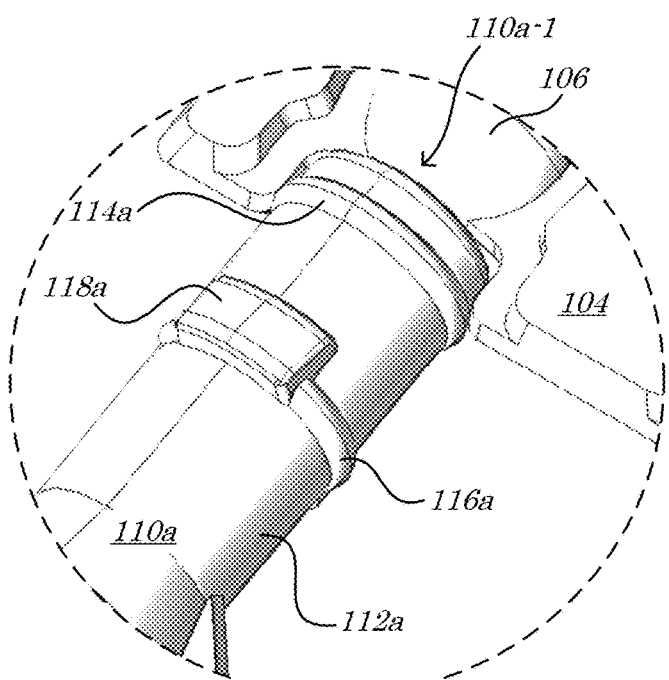

Referring initially to FIG. 1A and FIG. 1B, a perspective view of a BFS vial package 102 and a perspective close-up view of a portion of the BFS vial pack or package 102 according to some embodiments are shown. The BFS vial package 102 may, for example, comprise a plastic and/or other molded, extruded, and/or formed manifold 104. In some embodiments, the manifold 104 may comprise a plurality of attachment points 106 via which a plurality of BFS units, containers, and/or vials 110*a-e* are connected e.g., via a breakaway detachment design. FIG. 1B depicts an enlarged perspective view of the breakaway detachment design of a first BFS vial 110*a*. As shown, each BFS vial 110*a-e* may contain a single dose of fluid agent and, when a user is ready, a single vial such as the first BFS vial 110*a* may be removed from the manifold 104 via a tear-away type connection disposed between a first, outlet, or proximate end 110*a*-1 of the first BFS vial 110*a* (the proximate end 110*a*-1 being proximate to the manifold 104 and a second or distal end 110*a*-2 being distal therefrom) and the respective attachment point 106. According to some embodiments as depicted, for example, the proximate end 110*a*-1 (e.g., that may comprise and/or define an outlet; not separately labeled in FIG. 1A and FIG. 1B) of the first BFS vial 110*a* may be coupled to the manifold 104 at the attachment point 106. In some embodiments, by simply pulling the desired first BFS vial 110*a* away from the attachment point 106, a user is able to separate the first BFS vial 110*a* from the remaining BFS vials 110*b-e* and use only the single dose that is required and/or desired, rather than using a larger source of fluid agent (multiple dose syringe or vial; not shown), thereby completely preventing the risk of contaminating the single source of fluid agent disposed in the first BFS vial 110*a*.

According to some embodiments, each BFS vial 110*a-e* may comprise and/or define various features such as features molded, formed, cut, glued, and/or otherwise coupled thereto. As depicted in FIG. 1A and FIG. 1B, for example, the first BFS vial 110*a* may comprise a neck 112*a* (e.g., near the proximate end 110*a*-1) upon which various mating features are formed (or otherwise coupled). In some embodiments, the neck 112*a* may comprise a first exterior radial flange 114*a*, a second exterior radial flange 116*a*, and/or a mating tab 118*a*. According to some embodiments, the mating tab 118*a* may comprise a wedge-shaped radial protrusion (e.g., with an incline increasing from near the proximate end 110*a*-1 and towards the distal end 110*a*-2) disposed on, with, or as part of the second exterior radial flange 116*a*. In some embodiments, the first BFS vial 110*a* may comprise a fluid reservoir 120*a* in communication with the neck 112*a*. According to some embodiments, the fluid reservoir 120*a* may store, house, and/or accept the single dose of fluid and/or may be coupled to a grip plate 122*a*. The grip plate 122*a* may, for example, comprise a flat element that permits axial force to be applied to the first BFS vial 110*a* without causing such axial force to be applied to the fluid reservoir 120*a*.

In some embodiments, the package 102 may comprise an indicia imprinting on the manifold 104 itself and/or upon each individual BFS vial 110*a-e* (e.g., on the grip plate 122*a* of the first BFS vial 110*a*). Exemplary indicia may include, but is not limited to, lot number, expiration date, medication information, security stamp (color changing temperature sensor to provide indication of whether BFS vials 110*a-e* have or have not been maintained at required temperature), as well as the dose line provided on each BF vial 110*a-e*. While five (5) BFS vials 110*a-e* are depicted in FIG. 1A as being coupled to the manifold 104, fewer or more BFS vials 110*a-e* may be coupled to the manifold 104 as is or becomes desirable and/or practicable.

According to some embodiments, because BFS manufacturing tolerances are not as precise as injection molding and other manufacturing techniques, the configuration of the BFS vials 110*a-e*, such as including the first exterior radial flange 114*a*, the second exterior radial flange 116*a*, and/or the mating tab(s) 118*a*, may permit the BFS vials 110*a-e* to be coupled to a modular delivery system (not shown) as described herein, while enabling functionality despite a wide range of manufactured dimensions. In such a manner, for example, reduced costs may be achieved by employing BFS technology while maintaining modular fluid delivery functionality that previous systems could not achieve.

In some embodiments, fewer or more components 104, 106, 110*a-e*, 110*a*-1, 110*a*-2, 112*a*, 114*a*, 116*a*, 118*a*, 120*a*, 122*a* and/or various configurations of the depicted components 104, 106, 110*a-e*, 110*a*-1, 110*a*-2, 112*a*, 114*a*, 116*a*, 118*a*, 120*a*, 122*a* may be included in the BFS vial package 102 without deviating from the scope of embodiments described herein. In some embodiments, the components 104, 106, 110*a-e*, 110*a*-1, 110*a*-2, 112*a*, 114*a*, 116*a*, 118*a*, 120*a*, 122*a* may be similar in configuration and/or functionality to similarly named and/or numbered components as described herein. In some embodiments, the BFS vial package 102 (and/or portion and/or component 104, 106, 110*a-e*, 110*a*-1, 110*a*-2, 112*a*, 114*a*, 116*a*, 118*a*, 120*a*, 122*a* thereof) may be utilized in accordance with the methods 800, 900 of FIG. 8 and/or FIG. 9 herein, and/or portions or combinations thereof.

Figure 2A:
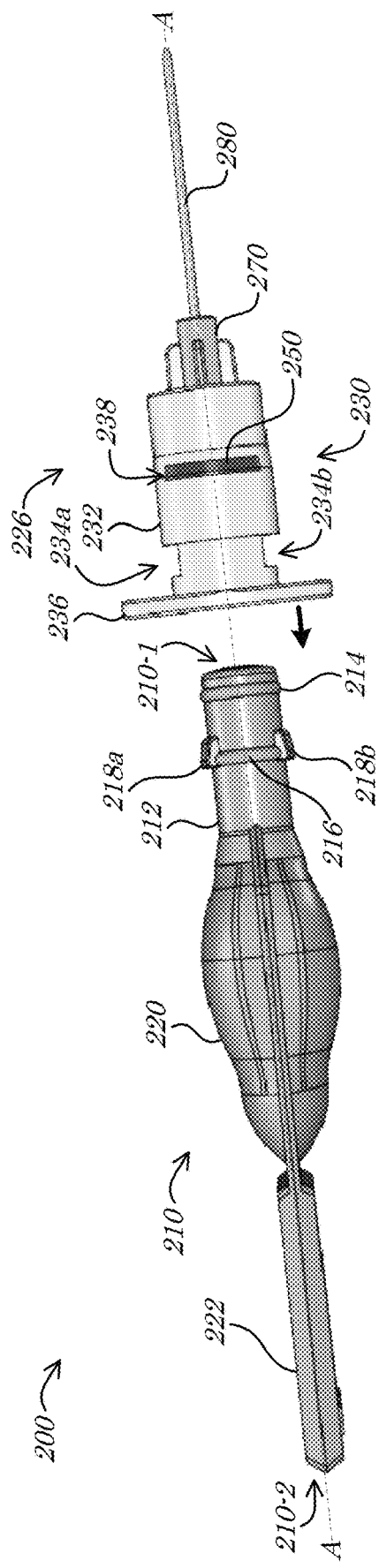
FIG. 2G is a right-side cross-sectional assembly view of the hub assembly of the fluid delivery system according to some embodiments.
FIG. 2H is a right-side cross-sectional view of the hub assembly of the fluid delivery system according to some embodiments.
FIG. 2I is a right-rear perspective cross-sectional view of the hub assembly of the fluid delivery system according to some embodiments.
FIG. 2J is a right-side perspective cross-sectional view of a portion of the fluid delivery system according to some embodiments.
FIG. 2K is a right-side cross-sectional view of a portion of the fluid delivery system according to some embodiments.
FIG. 2L is a right-front perspective cross-sectional view of a portion of the fluid delivery system according to some embodiments.
Figure 2B:
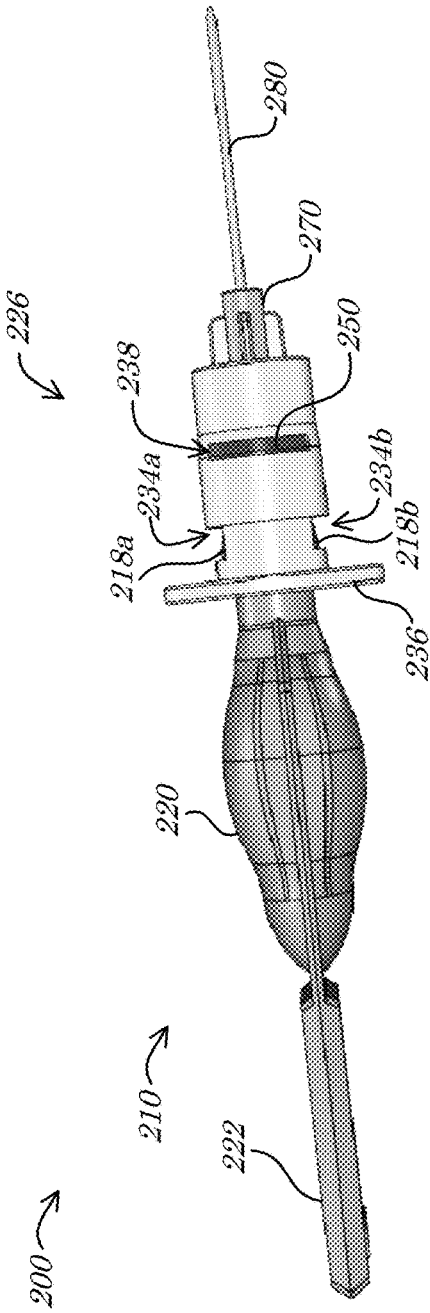
Figure 2C:
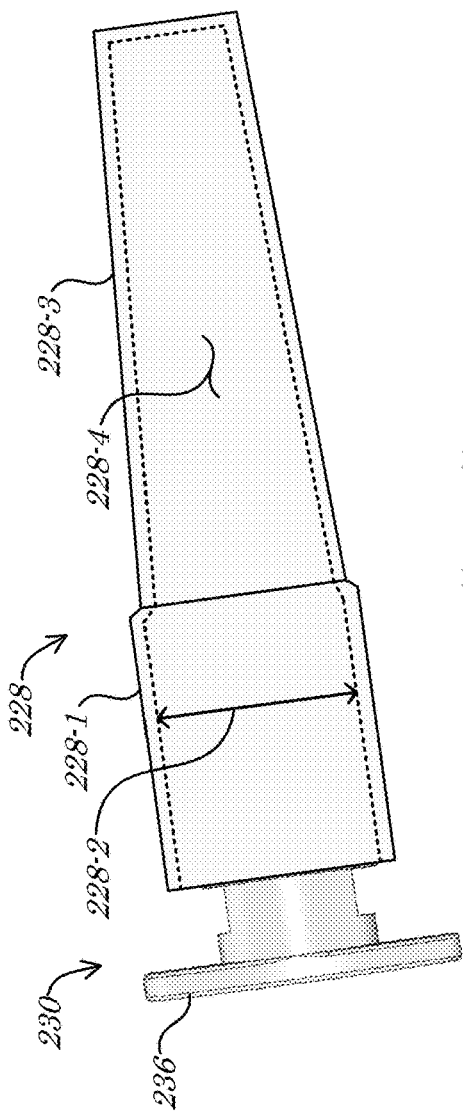
Figure 2D:
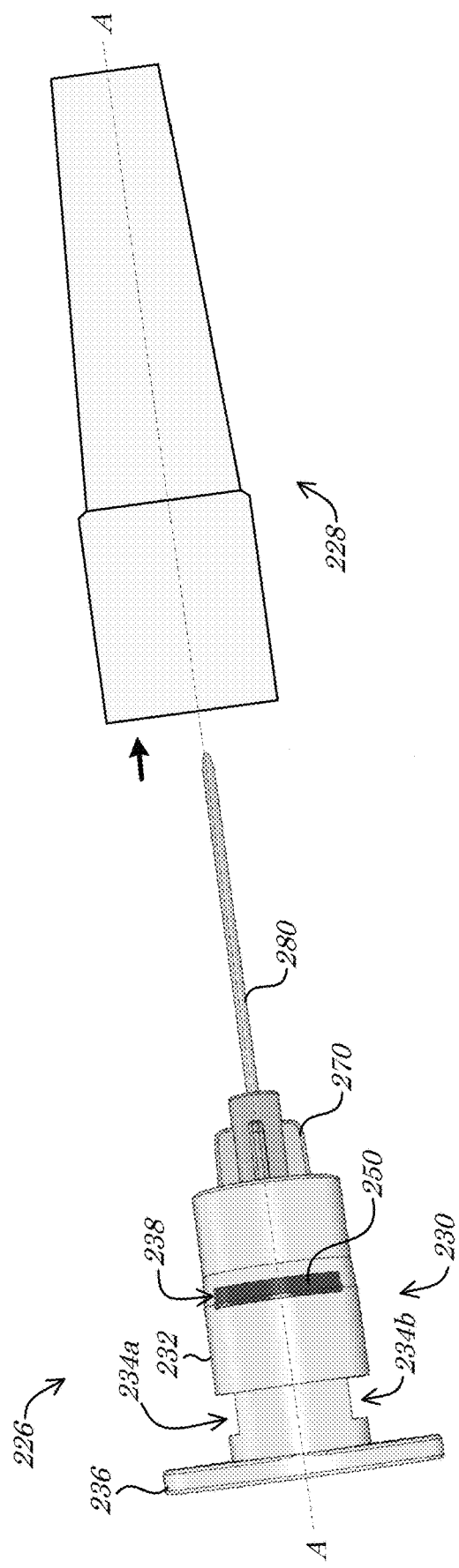
Figure 2E:
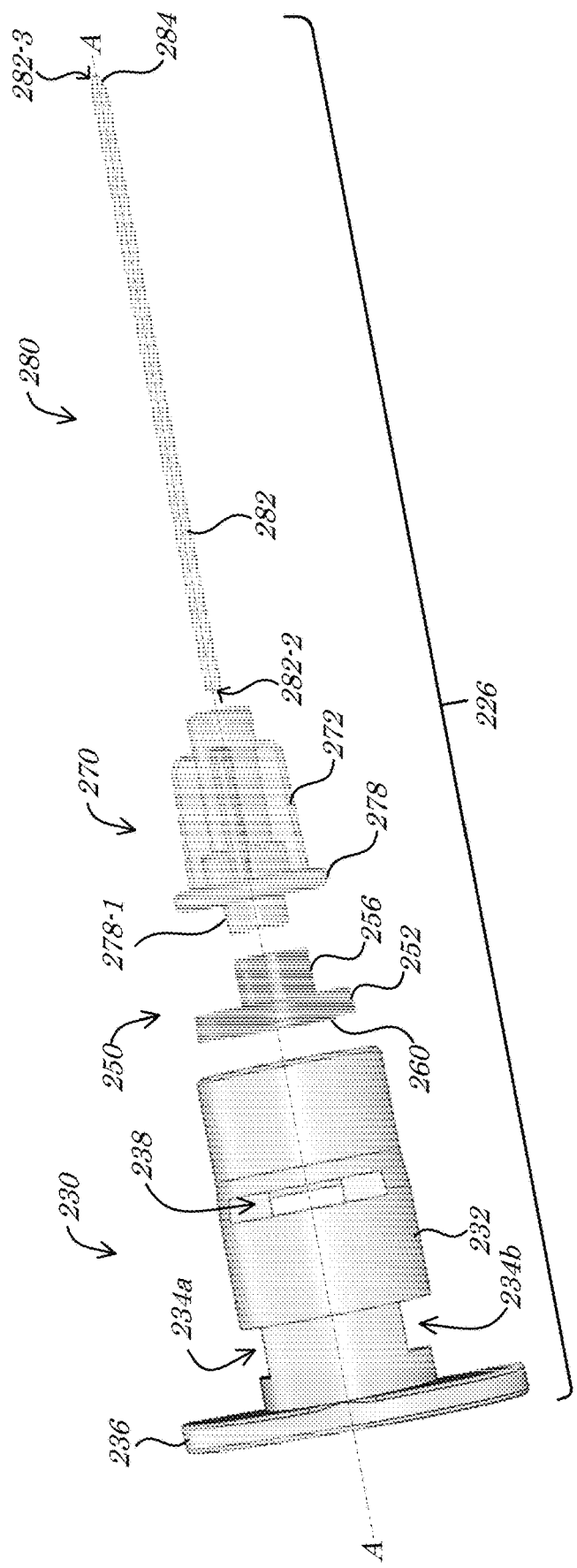
Figure 2H:
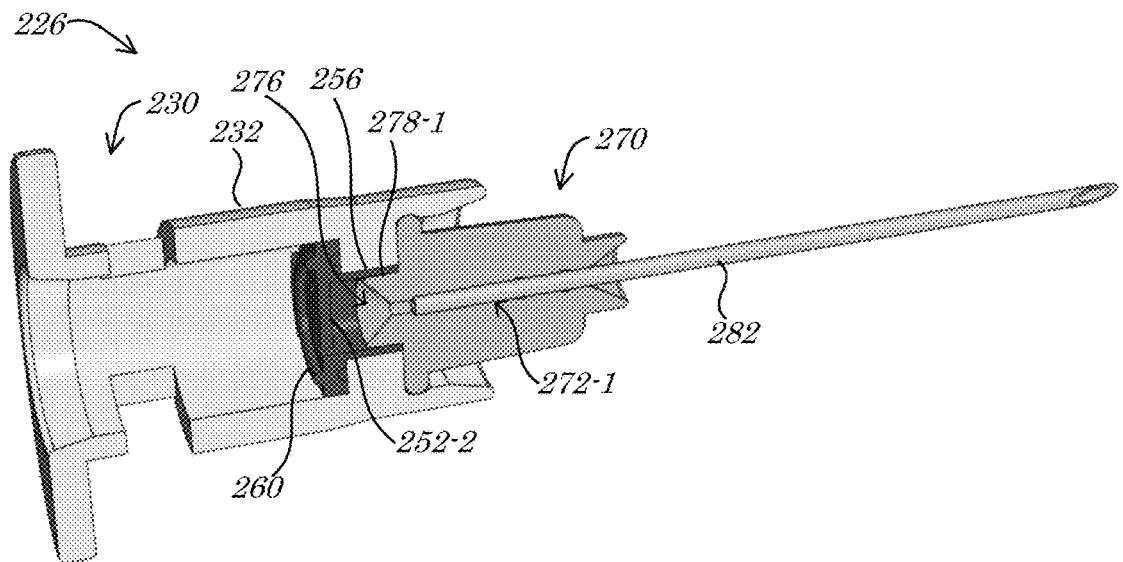
Figure 2I:
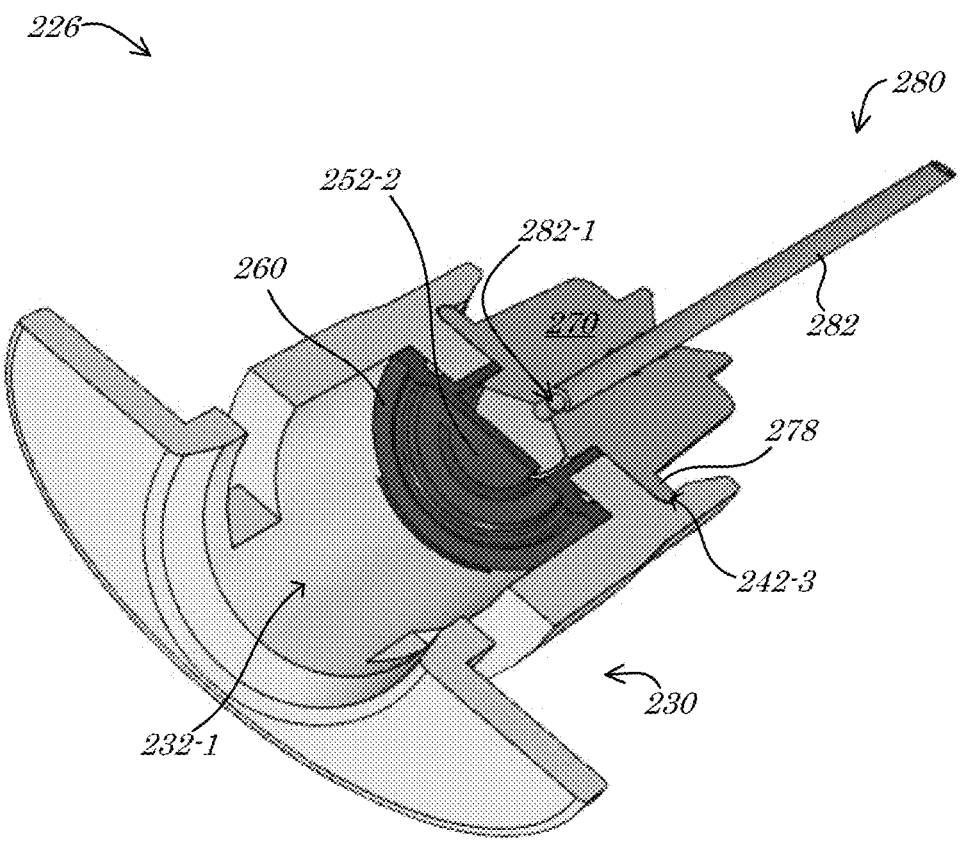
Figure 2J:
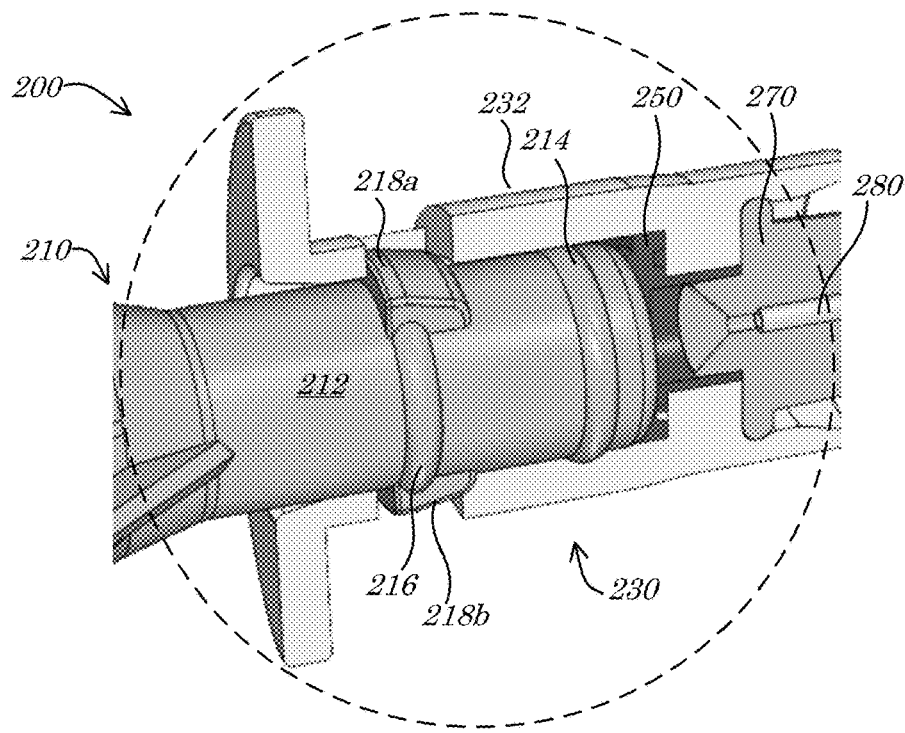
Figure 2K:
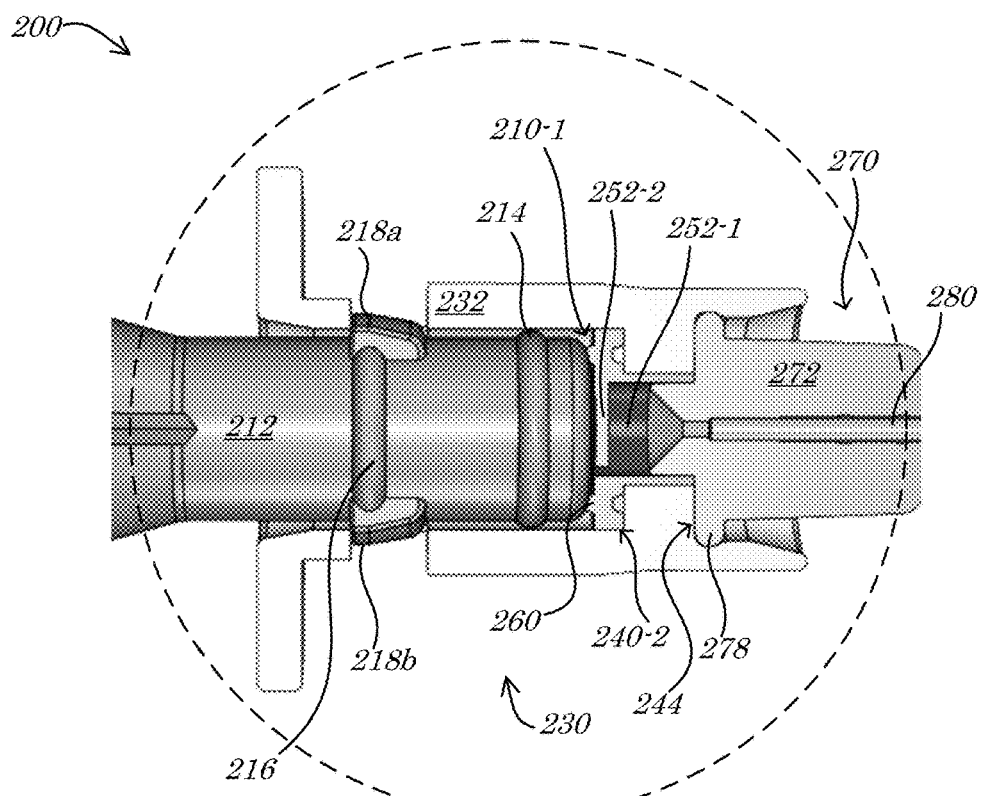
Figure 2L:
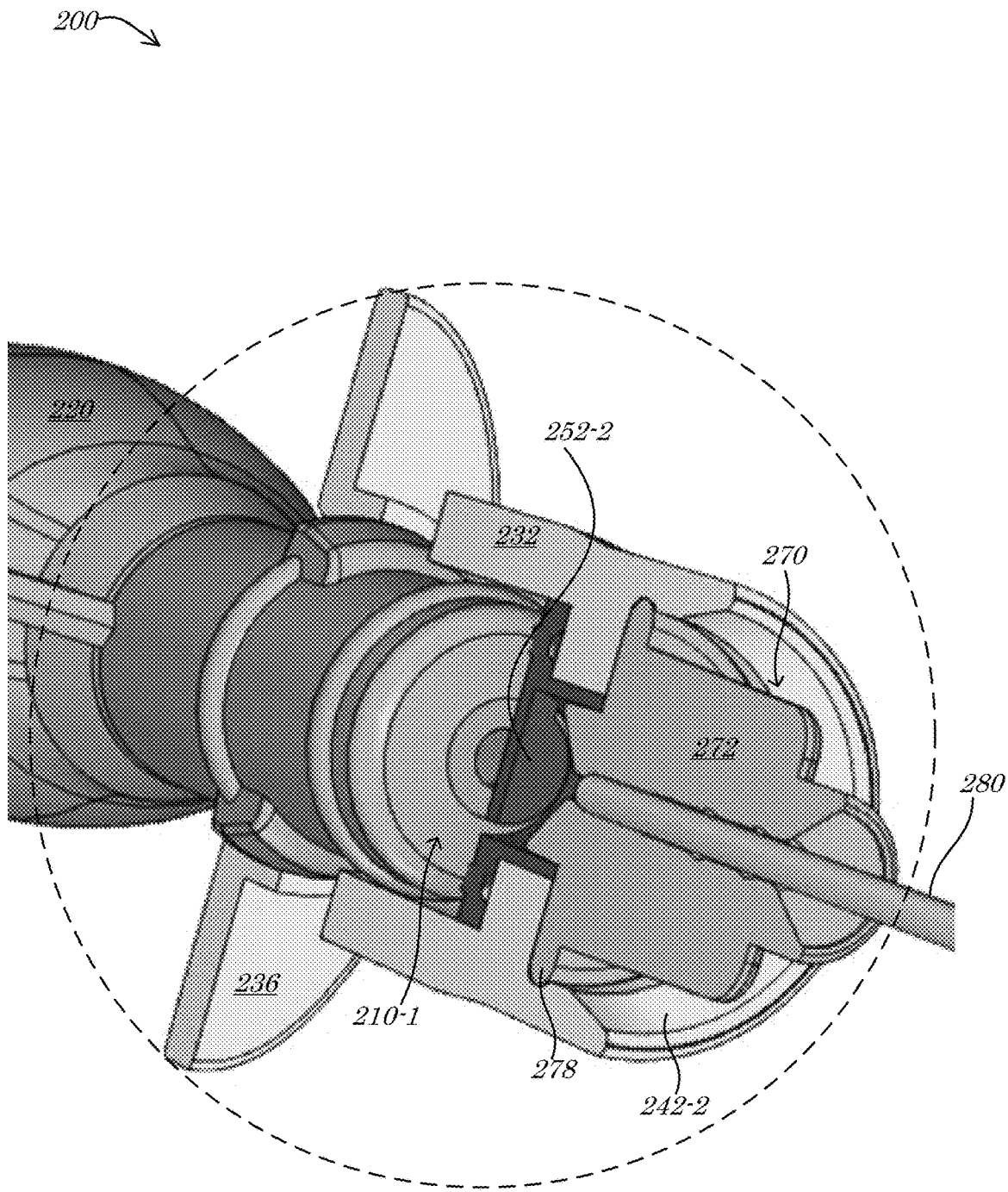

Turning now to FIG. 2A, FIG. 2B, FIG. 2C, FIG. 2D, FIG. 2E, FIG. 2F, FIG. 2G, FIG. 2H, FIG. 2I, FIG. 2J, FIG. 2K, and FIG. 2L, various views of a fluid delivery system 200 according to some embodiments are shown. In particular, FIG. 2A and FIG. 2B are right-side views of the fluid delivery system 200, FIG. 2C and FIG. 2D are right-side views of a portion of the fluid delivery system 200, FIG. 2E is an exploded right-side view of a portion of the fluid delivery system 200, FIG. 2F is a right-side cross-sectional view of the fluid delivery system 200, FIG. 2G is a right-side cross-sectional assembly view of a portion of the fluid delivery system 200, FIG. 2H is a right-side cross-sectional view of a portion of the fluid delivery system 200, FIG. 2I is a right-rear perspective cross-sectional view of a portion of the fluid delivery system 200, FIG. 2J is a right-side perspective cross-sectional view of a portion of the fluid delivery system 200, FIG. 2K is a right-side cross-sectional view of a portion of the fluid delivery system 200, and FIG. 2L is a right-front perspective cross-sectional view of a portion of the fluid delivery system 200.

In some embodiments, the fluid delivery system 200 may comprise various inter-connected and/or modular components such as a BFS vial 210 (e.g., having a first end 210-1 and a second end 210-2) comprising and/or defining a vial neck 212, a first flange 214, a second flange 216, a plurality of locking tabs 218*a-b*, a collapsible reservoir 220, and/or a grip plate 222. According to some embodiments, the fluid delivery system 200 may comprise a delivery or hub assembly 226 comprising a safety cover or cap 228 (e.g., comprising and/or defining a cylindrical cap body 228-1, an interior void 228-2, a tapered cap body 228-3, and/or head space 228-4), a hub 230 (e.g., comprising a hub body 232, a hub bore 232-1 defining a hub bore diameter 232-2, a vial bevel 232-3, a plurality of locking slots 234*a-b*, an assembly flange 236, a valve slot 238, a fluid outlet bore 240 defining a fluid outlet bore diameter 240-1, a valve seat 240-2, an insert bore 242 defining an insert bore diameter 242-1, an insert bevel 242-2, an insert recess 242-3, and/or an insert seat 244), a valve 250 (e.g., comprising and/or defining a valve body 252, a valve channel 252-1, a valve flap 252-2, a mounting wing 254*a*, a riser 256, an antegrade void 258, a vial flange 260, and seating surface 262), an insert 270 (e.g., comprising and/or defining an insert body 272, a fluid channel 272-1, a channel stop 272-2, an outlet funnel 274, an inlet funnel 276, a seating flange 278, and/or a seating flange collar 278-1), and/or an administration member 280

(e.g., comprising and/or defining an elongate body 282, a fluid bore 282-1, a first end 282-2, a second end 282-3, and/or a needle, point, or tip 284). According to some embodiments, the fluid delivery system 200 and/or the hub assembly 226 may include a modular design consisting of separately constructed components 228, 230, 250, 270, 280 cooperatively arranged and coupled to one another. The components 228, 230, 250, 270, 280 of the hub assembly 226 may include, for example, the hub 230 being configured to be coupled to a source containing the fluid agent, including, but not limited to, the BFS vial 210, a one-way valve 250 positioned within the hub 230 and configured to limit fluid flow to an antegrade direction, and the insert 270 positioned within the hub 230 and configured to receive and retain the administration member 280 for receiving the fluid agent from the BFS vial 210 and administering the fluid agent into a patient (not shown).

In some embodiments, the administration member 280 may include the needle 284 for at least one of subcutaneous, intramuscular, intradermal, and intravenous injection of the fluid agent into the patient. For ease of explanation and description, the figures and the description herein generally refer to the administration member 280 as a needle 284. However, it should be noted that, in other embodiments, the administration member 280 may include a nozzle (not shown) configured to control administration of the fluid agent to the patient. The nozzle may include a spray nozzle, for example, configured to facilitate dispersion of the fluid agent into a spray. Accordingly, a hub assembly 226 fitted with a spray nozzle may be particularly useful in the administration of a fluid agent into the nasal passage, for example, or other parts of the body that benefit from a spray application (e.g., ear canal, other orifices). In other embodiments, the nozzle may be configured to facilitate formation of droplets of the fluid agent. Thus, a hub assembly 226 including a droplet nozzle may be useful in the administration of a fluid agent by way of droplets, such as administration to the eyes, topical administration, and the like.

As generally understood, the fluid agent may include any type of agent to be injected into a patient (e.g., mammal, either human or non-human) and capable of producing an effect. Accordingly, the agent may include, but is not limited to, a vaccine, a drug, a therapeutic agent, a medicament, or the like.

According to some embodiments, the hub 230 may include a hub body 232 defining a hub bore 232-1 having a first end defining an inlet port and a second end defining an outlet, e.g., along an axis "A-A" as depicted in FIG. 2E. In some embodiments, the hub bore 232-1 may provide a fluid pathway between the inlet and outlet ports. The hub 230 may include a specialty, non-standard (non-Luer-type) connection fitting such as the locking slots 234a-b configured to be coupled with a corresponding specialty, non-standard connection fitting of the BFS vial 210 (shown in FIG. 2A and FIG. 2F) such as the locking tabs 218a-b. For example, a portion of the hub body 232 adjacent the first end may include recesses, depressions, or complete apertures (e.g., the locking slots 234a-b) of a particular shape or geometry which are shaped and/or sized to receive correspondingly shaped and/or sized protrusions, projections, or the like (e.g., the locking tabs 218a-b) of the BFS vial 210. In some embodiments, the hub body 232 may include two locking slots 234a-b defining opposing apertures on either side of the hub body 232 and adjacent to the first end, the locking slots 234a-b being shaped and/or sized to receive and retain corresponding locking tabs 218a-b defined on the neck 212 of a BFS vial 210. According to some embodiments, the hub 230 may comprise one or more window or port portions such as the valve slot 238 formed on the hub body 232 and configured to provide a means for receiving and retaining a portion (e.g., the mounting wing 254a) of the valve 250 within.

For example, the valve 250 may be generally positioned within the hub bore 232-1 and/or may be formed from a polymer material, such rubber, synthetic rubber, latex, and/or other elastomeric polymer material. In some embodiments, the valve 250 may be press-fit into the hub bore 232-1 such that portions (e.g., the mounting wing 254a) of the valve 250 may extend through the valve slot(s) 238 and fill in any gaps so as to provide at least a watertight seal. The exposed one or more portions of the valve 250 (and/or of the mounting wing 254a thereof) extending to the outer surface of the hub 230 through the valve slot(s) 238 may generally provide a friction fit for an interior surface interior void 228-2 of the cap 228 in the case that the cap 228 is placed over and/or coupled to the hub assembly 226. In other words, the exposed polymer material of the valve 250 (and/or of the mounting wing 254a thereof) may generally provide sufficient friction with the cap 228 so as to keep the cap 228 retained on to the hub assembly 226. In some embodiments, the valve 250 may comprise and/or define a valve channel 252-1 extending therethrough and in coaxial alignment with the hub bore 232-1, e.g., along axis "A-A". According to some embodiments, the valve 250 may comprise a valve flap 252-2 provided within the valve channel 252-1 and configured to limit fluid flow to an antegrade direction from the hub 230 towards the administration member 280, thereby ensuring that fluid flows in a single direction when the fluid agent is delivered from the BFS vial 210.

In some embodiments, the insert 270 may be positioned within the hub bore 232-1 adjacent to the second end of the hub 230. The insert 270 may, according to some embodiments, comprise and/or define a fluid channel 272-1 extending entirely axially through the insert 270. The fluid channel 272-1 may be in coaxial alignment with the hub bore 232-1 and/or the valve channel 252-1, e.g., along axis "A-A", such that a fluid pathway extends entirely from the first end of the hub 230, through the hub bore 232-1, through the valve channel 252-1 of the valve 250, and through fluid channel 272-1 of the insert 270. According to some embodiments, the seating flange collar 278-1 of the insert 270 may be configured to be fitted within the valve channel 252-1, e.g., in the riser 256. The administration member 280 (e.g., needle 284) may, in some embodiments, be received and/or retained within the fluid channel 272-1 of the insert 270, such that, upon delivery of the fluid agent from the BFS vial 210 and through the fluid pathways of the hub assembly 226, the fluid agent will flow out of the fluid bore 282-1 of the needle 284, thereby allowing for delivery of the fluid agent to the patient.

According to some embodiments, the hub assembly 226 may include the cap 228 for covering the needle 284 to prevent contamination and further reduce the risk of needlestick injuries, and thus reduce the potential for spreading blood-borne diseases. In some embodiments, the hub assembly 226 may generally be packaged and delivered in a fully assembled state, including the cap 228 provided over the needle 284. Accordingly, a user does not have to deal with an exposed needle 284 when first attaching the BFS vial 210 to the hub assembly 226. Rather, the user need only remove the cap 228 once the BFS vial 210 has been securely attached to the hub assembly 226 to thereby expose the needle 284 for fluid agent delivery. The user may then replace the cap 228 once delivery is complete.

In some embodiments, the hub 230, the valve 250, the insert 270, and/or the cap 228, may be composed of a medical grade material. In some embodiments, the hub 230, the insert 270, and/or cap 228, may be composed of a thermoplastic polymer, including, but not limited to, polypropylene, polyethylene, polybenzimidazole, acrylonitrile butadiene styrene (ABS) polystyrene, polyvinyl chloride, PVC, or the like.

Referring to FIG. 2A and FIG. 2B, right-side views of the fluid delivery system 200 illustrate attachment of the BFS vial 210 to the hub assembly 226. As shown in an unassembled state in FIG. 2A, for example, the hub assembly 226 may be urged axially along the axis "A-A" (e.g., to the left in FIG. 2A) in accordance with the arrow such that it engages with and/or becomes selectively indexed and/or coupled to the BFS vial 210. In some embodiments, the BFS vial 210 may define the collapsible reservoir 220 that may generally include a flexible body having an interior volume sufficient to contain at least one dose of the fluid agent within. The BFS vial 210 may, in some embodiments, comprise the neck 212 extending from the body of the collapsible reservoir 220 and terminating at the first end 210-1 defining an outlet for dispensing the fluid agent upon squeezing of the body of the collapsible reservoir 220 (e.g., in accordance with the radially inward-pointing arrows of FIG. 2F). According to some embodiments, the BFS vial 210 may be formed by BFS technology. BFS technology is a manufacturing technique used to produce liquid-filled containers. The BFS vial 210 may be formed by BFS technology, in that the collapsible reservoir 220, the neck 212, and first and second ends 210-1, 210-2 are formed, filled within a fluid agent, and sealed in a continuous process without human intervention, in a sterile enclosed area inside a machine. Accordingly, this process can be used to aseptically manufacture sterile pharmaceutical liquid dosage forms. BFS technology may be particularly attractive in the market, as it reduces personnel intervention making it a more robust method for the aseptic preparation of sterile pharmaceuticals.

According to some embodiments, the hub body 232 may generally include a specialty, non-standard connection fitting (locking slots 234a-b) configured to be coupled with a corresponding specialty, non-standard connection fitting (e.g., locking tabs 218a-b) of the BFS vial 210. For example, the BFS vial 210 may include the two (2) locking tabs 218a-b defined on opposing sides of the neck 212 adjacent to the first end 210-1 and having a general shape corresponding to the locking slots 234a-b on the hub 230. Upon a user inserting the first end 210-1 of the BFS vial 210 into the hub 230, the locking tabs 218a-b may be shaped (e.g., wedge-shaped) so as to slide into engagement with the corresponding locking slots 234a-b, respectively, such engagement as illustrated in FIG. 2B and FIG. 2F. FIG. 2F is a perspective view, partly in section, illustrating the BFS vial 210 attached to the hub assembly 226 and showing engagement between the connection fittings (e.g., locking tabs 218a-b and locking slots 234a-b) of the BFS vial 210 and the hub 230 of the hub assembly 226, respectively. As depicted, the locking tabs 218a-b on the neck 212 of the BFS vial 210 may be in engagement with the corresponding locking slots 234a-b of the hub 230. In some embodiments, the locking tabs 218a-b may be shaped to prevent or inhibit withdrawal of the BFS vial 210 from the hub 230, thereby effectively locking themselves within the locking slots 234a-b and effectively locking the BFS vial 210 into engagement with the hub assembly 226. By securing the BFS vial 210 to the hub assembly 226, a user need only apply force to (e.g., squeeze) the collapsible reservoir 220, e.g., as indicated by the arrows in FIG. 2F, to cause the fluid agent to flow along the axis "A-A" and out of the fluid bore 282-1 at the needle 284, the fluid agent traveling from the BFS vial 210, through the hub assembly 226 including through the needle 284, and into the patient (not shown).

In some embodiments, a specialty, non-standard connection fitting between the hub assembly 226 and the BFS vial 210 allows for only approved sources (e.g., single-dose BFS vials 210) with a corresponding agent to be used with the fluid delivery system 200, thereby adding a layer of security. For example, a method of delivery is generally dependent on the type of fluid agent to be delivered. For example, some medicaments are best delivered intravenously while some vaccines are best delivered intradermally, and yet still, some fluid agents are administered via droplets or spray. Accordingly, the hub assembly 226 may be configured for delivery of a specific fluid agent and thus the connection fitting on the hub assembly 226 may be designed so as to only accept and engage a corresponding connection fitting of a BFS vial 210 containing that specific fluid agent. Accordingly, the specialty connection fitting design may ensure that only the matching BFS vial 210 (which contains the correct fluid agent for that specific delivery assembly) is able to be connected to the hub assembly 226, thereby ensuring safety and reducing risk.

FIG. 2G is an exploded, perspective sectional view of the hub assembly 226. FIG. 2H is a perspective sectional view of the hub assembly 226 illustrating the components assembled to one another and forming a continuous fluid pathway there-between and FIG. 2I is another perspective sectional view of the hub assembly 226 illustrating the components assembled to one another. As shown, and in accordance with some embodiments, the hub 230 may comprise and/or define the hub bore 232-1 extending therethrough. The hub 230 may also or alternatively comprise a fluid outlet bore 240 to which the valve 250 and insert 270 are coupled. In some embodiments, the riser 256 of the valve 250 may be positioned on one side of the fluid outlet bore 240 (e.g., on the left side as-depicted) and the seating flange collar 278-1 of the insert 270 may generally protrude through or into the fluid outlet bore 240 (and/or through or into the riser 256 of the valve 250) and may be positioned on the other side of the fluid outlet bore 240 (e.g., on the right side as-depicted). According to some embodiments, the seating flange collar 278-1 of the insert 270 may be received within the valve channel 252-1 of the riser 256 of the valve 250 and extend may generally abut the valve flap 252-2. In some embodiments, the administration member 280 comprises the elongate body 282 which may be hollow and/or otherwise define the fluid bore 282-1, and/or may comprise a generally blunt second end 282-3 and the piercing tip 284 at the first end 282-2. In some embodiments, the second end 282-3 of the administration member 280 may be positioned within the fluid channel 272-1 of the insert 270, wherein the fluid channel 272-1 may comprise the channel stop 272-2 or end portion (e.g., interior flange or tapered to a decreasing diameter) which prevents the second end 282-3 of the administration member 280 from traveling too far down the fluid channel 272-1. Once fully assembled, a fluid pathway may extend entirely through the hub assembly 226, from the hub 230 to the tip 284 of the administration member 280, and passing through each of the components therebetween (e.g., through the hub 230, the valve 250, and the insert 270).

FIG. 2J is an enlarged, perspective view, partly in section, illustrating the locking engagement between the connection fittings of the BFS vial 210 and the hub 230 of the hub assembly 226. In some embodiments, the hub body 232 may generally include a specialty, non-standard connection fitting (locking slots 234a-b) configured to be coupled with a corresponding specialty, non-standard connection fitting of the BFS vial 210. For example, the BFS vial 210 may include two (2) locking tabs 218a-b and/or other protrusions or features defined on opposing sides of the neck 212 adjacent to the first end 210-1 and having a general shape corresponding to the locking slots 234a-b on the hub 230. Upon a user inserting the first end 210-1 of the BFS vial 210 into the hub 230, the locking tabs 218a-b may be shaped so as to slide into engagement with the corresponding locking slots 234a-b, respectively. As shown, the locking tabs 218a-b on the neck of the BFS vial 210 may be in engagement with the corresponding locking slots 234a-b of the hub 230. The locking tabs 218a-b may, in some embodiments, be further shaped to prevent withdrawal of the BFS vial 210 from the hub 230, thereby effectively locking themselves within the locking slots 234a-b and effectively locking the BFS vial 210 into engagement with the hub assembly 226.

FIG. 2K and FIG. 2L are enlarged, perspective views, partly in section, illustrating engagement between the first end 210-1 (and outlet) of the BFS vial 210 with the valve 250 of the hub assembly 226 when the BFS vial 210 is securely coupled to the hub assembly 226. By securing the BFS vial 210 to the hub 230, the outlet of the first end 210-1 of the BFS vial 210 is, according to some embodiments, disposed in direct alignment (e.g., axial alignment) with the valve flap 252-2 of the valve 250. Accordingly, the outlet of the BFS vial 210 may be in direct axial alignment with the fluid pathway (e.g., along axis "A-A"). It should be noted that, due to some minor variations that commonly occur during the BFS manufacturing process, BFS vial dimensions may be imprecise. For example, the second end 210-1 of any given BFS vial 210 may have different dimensions when compared to one another (on a microscale). In order to compensate for such variation, connection fittings between the BFS vial 210 and the hub 230 further ensure that the first end 210-1 of the BFS vial 210 is positioned against and into engagement with the valve 250 (e.g., the vial flange 260 thereof). In some embodiments, due to the polymer material of the valve 250, a seal may be created between the first end 210-1 of the BFS vial 210 and the vial flange 260 of the valve 250, thereby accounting for any imprecise manufacturing of the BFS vial 210.

According to some embodiments, and as depicted in FIG. 2A, the fluid delivery system 200 may be assembled by application of opposing axial forces that urge the hub assembly 226 onto the BFS vial 210 (in accordance with the arrow shown). In some embodiments, a user (not shown) may take hold of the grip plate 222 and the hub 230 (and/or the cap 228) and push the BFS vial 210 into the hub bore 232-1 of the hub assembly 226. The grip plate 222 may permit the user to apply an axial force in the direction of the hub assembly 226 without requiring force to be applied to the collapsible reservoir 220 (e.g., preventing accidental expelling of the fluid stored in the collapsible reservoir 220). According to some embodiments, the user may apply axial force to the assembly flange 236 of the hub 230 and an opposing axial force to the grip plate 222, causing a coupling or mating of the BFS vial 210 with the hub assembly 226, e.g., as depicted in FIG. 2B.

Referring to FIG. 2C and FIG. 2D, the cap 228 may be selectively engaged to couple to the hub assembly 226. The hub assembly 226 may be disposed in the interior void 228-2 of the cylindrical cap body 228-1, for example, and/or the administration member 280 thereof may be disposed in the head space 228-4 of the tapered cap body 228-3, such that the needle 284 is protected and/or shrouded—e.g., for cleanliness and safety. In some embodiments, an outside diameter of the hub body 232 may be sized to fit within the interior void 228-2 (e.g., may be configured with an outside diameter that is smaller than an inside diameter of the interior void 228-2). According to some embodiments, one or more portions of the valve 250 may extend through the side of the hub body 232 causing a localized increase in outside diameter of the hub assembly 226. In some embodiments, this localized maximum outside diameter of the hub assembly 226 may be configured to provide a transition fit (e.g., an "H7/j6" or "tight fit") between the hub body 232 and the cap 228, allowing the cap 228 to be selectively removed (e.g., as depicted in FIG. 2D) and/or installed by hand, as desired. According to some embodiments, such as in the case that the valve 250 comprises rubber or another frictional surface, the friction coefficient of such material and/or a compression of the material inside of the interior void 228-2 may provide and/or enhance the nature of the fit.

According to some embodiments, and as depicted in the assembly view of FIG. 2E, the fluid delivery system 200 may comprise a hub assembly 226 that is composed of a plurality of modular components such as the hub 230, the valve 250, the insert 270, and the administration member 280. As depicted in FIG. 2F, the modular components 230, 250, 270, 280 may be coupled together and attached to a BFS vial 210 to form the fluid delivery system 200. As depicted in the cross-sectional assembly view of FIG. 2G, the modular components 230, 250, 270, 280 may be assembled along an axis "A-A" by alignment and/or coupling of various portions and/or features thereof. The hub 230 may comprise the hub body 232 (which may be substantially cylindrical in some embodiments) that may comprise and/or define the hub bore 232-1 having an inside hub bore diameter 232-2, and/or may define a vial bevel 232-3 that engages with the BFS vial 210 upon insertion thereof. The first flange 214 of the BFS vial 210 and/or the locking tabs 218a-b may, for example, extend radially outward beyond the hub bore diameter 232-2 and may accordingly engage with the side walls of the hub bore 232-1 as they are inserted deeper into the vial bevel 232-3. In some embodiments, such engagement may cause the neck 212 of the BFS vial 210 (and/or the first flange 214 and/or the locking tabs 218a-b thereof) to compress radially inward and/or may cause the hub body 232 to expand radially outward (e.g., elastically), to allow continued advancement of the BFS vial 210 into the hub 230, e.g., in accordance with a tight fit and/or interference fit engagement. According to some embodiments, the radial pressure exerted by forcing the neck 212 of the BFS vial 210 into the hub 230 may impart a radial spring effect to the locking tabs 218a-b such that when axial advancement aligns the locking tabs 218a-b with the corresponding locking slots 234a-b, the locking tabs 218a-b spring radially outward and into the corresponding locking slots 234a-b, thereby reducing and/or removing the radial pressure exerted thereon by the difference between the interior hub bore diameter 232-2 and the outside diameter and/or radial extents of the locking tabs 218a-b.

In some embodiments, the hub 230 may comprise the fluid outlet bore 240 having a fluid outlet bore diameter 240-1. According to some embodiments, as-depicted in FIG. 2G, the fluid outlet bore diameter 240-1 may be smaller than the hub bore diameter 232-2. The difference in the fluid outlet bore diameter 240-1 and the hub bore diameter 232-2 may, for example, provide for and/or define the valve seat 240-2 and/or the insert seat 244. In some embodiments, the valve 250 may be inserted into the hub bore 232-1 and may comprise the valve body 252 having an outside diameter sized to fit within the hub bore 232-1. According to some embodiments, the diameter of the valve body 252 may be larger than the hub bore diameter 232-2 such that the valve 250 must be compressed for an interference fit into the hub bore 232-1. According to some embodiments, the valve 250 may be seated into the valve seat 240-2 and/or the mounting wing 254a may be engaged to fit within and/or through the valve slot 238 in the side wall of the hub body 232, e.g., creating a water-tight seal between the valve body 252 and the hub body 232. In some embodiments, the hub 230 may comprise the insert bore 242 having an insert bore diameter 242-1. According to some embodiments, the insert 270 may comprise the seating flange 278 that may have an outside diameter larger than the inside diameter of the insert bore 242-1. Axial advancement or insertion of the insert 270 into the insert bore 242 may accordingly cause the seating flange 278 to engage the insert bevel 242-2 of the hub 230, which may exert a radially outward force on the insert bevel 242-2 that may cause the hub body 232 to expand (e.g., elastically) radially to accommodate the seating flange 238. In some embodiments, the insert recess 242-3 of the hub 230 may be sized to accommodate the seating flange 238 and accordingly, upon advancement of the insert 270 into the insert bore 242 such that the seating flange 238 aligns axially with the insert recess 242-3, the insert 270 may snap into place and the hub body 232 may return to the original diameter thereof. According to some embodiments, the seating flange 278 and/or the seating flange collar 278-1 may engage with and/or create a water-tight seal with the insert seat 244 in the case that the seating flange 238 is seated in the insert recess 242-3. In some embodiments, the insert 270 may comprise the inlet funnel 276 configured to funnel fluid traveling in an antegrade direction into the fluid channel 272-1. According to some embodiments, the administration member 280 may be inserted into the insert 270 by entering the outlet funnel 274 and extending into the fluid channel 272-1 up to the channel stop 272-2.

Referring to FIG. 2H and FIG. 2I, the seating and sealing between the hub 230, the valve 250, and the insert 270 is depicted. In FIG. 2H, for example, the seating flange collar 278-1 of the insert 270 is shown having a smaller outside diameter than the inside diameter of the valve channel 252-1 in the riser 256 of the valve 250, and in the case that the seating flange 238 is seated in the insert recess 242-3, the seating flange collar 278-1 is disposed within the valve channel 252-1 in the riser 256 of the valve 250. In some embodiments, the fit between the seating flange collar 278-1, the riser 256, and the fluid outlet bore 240 may be configured to provide for a water-tight seal such that any fluid directed axially through the valve 250 in an antegrade direction must pass into the inlet funnel 276 and through the fluid bore 282-1 of the administration member 280. As depicted in FIG. 2H and FIG. 2I in accordance with some embodiments, the valve flap 252-2 may comprise a pliant portion of the valve 250 centered in the path of fluid flow and being free to bend in an antegrade direction by being unencumbered due to free space provided between the valve flap 252-2 and the inlet funnel 276 of the insert 270 and/or may be permitted to travel into the inlet funnel 276 itself.

Referring to FIG. 2J and FIG. 2K, the mating and/or sealing between the BFS vial 210 and the hub assembly 226 is shown. The first flange 214 of the BFS vial 210 is depicted having an outside diameter and/or radial extent equal to or greater than the hub bore diameter 232-1, for example, thus creating a fluid-tight seal within the hub bore 232. The second flange 216 and/or the locking tabs 218a-b are depicted as being seated in the hub 230 and as being shaped to prevent retrograde axial movement of the BFS vial 210 with respect to the hub 230, by having features that project radially outward to engage with the side walls of the hub body 232. In some embodiments as-depicted, the spatial configuration of the locking tabs 218a-b and the hub bore 232 may cause the first end 210-1 of the BFS vial 210 to contact, coupled with, and/or seat against the vial flange 260 of the valve 250, thereby creating a fluid-tight seal therebetween. According to some embodiments, the valve 250 may create a seal with the valve seat 240-2 and/or the insert 270 (and/or the seating flange 238 thereof) may create a seal with the insert seat 244. In some embodiments, the valve flap 252-1 may be positioned over and/or biased against the first end 210-1 of the BFS vial 210 such that it prevents any retrograde flow of fluid into the BFS vial 210. The first end 210-1 of the BFS vial 210 may, as positioned against the valve 250 and seated in the vial flange 260 in FIG. 2K for example, prevent retrograde movement or axial displacement of the valve flap 252-2 in the direction of the BFS vial 210, thereby preventing any opening in the first end 210-1 of the BFS vial 210 from being uncovered in response to a any retrograde force (while the valve flap 252-2 is otherwise free to bend or move in an antegrade direction at least by not being blocked by any objects in the valve channel 252-1. Such a configuration in accordance with some embodiments is depicted in FIG. 2L, where the collapsible reservoir 220 may provide fluid via the first end 210-1 of the BFS vial 210 by such fluid flow forcing an antegrade displacement of the hinged/flapped valve flap 252-2, while a retrograde flow would not be possible by nature of the first end 210-1 of the BFS vial 210 blocking or preventing retrograde displacement of the valve flap 252-2.

In some embodiments, fewer or more components 210, 210-1, 210-2, 212, 214, 216, 218a-b, 220, 222, 226, 228, 228-1, 228-2, 228-3, 228-4, 230, 232, 232-1, 232-2, 232-3, 234a-b, 236, 238, 240, 240-1, 240-2, 242, 242-1, 242-2, 242-3, 244, 250, 252, 252-1, 252-2, 254a, 256, 258, 260, 262, 270, 272, 272-1, 272-2, 274, 276, 278, 278-1, 280, 282, 282-1, 282-2, 282-3, 284 and/or various configurations of the depicted components 210, 210-1, 210-2, 212, 214, 216, 218a-b, 220, 222, 226, 228, 228-1, 228-2, 228-3, 228-4, 230, 232, 232-1, 232-2, 232-3, 234a-b, 236, 238, 240, 240-1, 240-2, 242, 242-1, 242-2, 242-3, 244, 250, 252, 252-1, 252-2, 254a, 256, 258, 260, 262, 270, 272, 272-1, 272-2, 274, 276, 278, 278-1, 280, 282, 282-1, 282-2, 282-3, 284 may be included in the fluid delivery system 200 without deviating from the scope of embodiments described herein. In some embodiments, the components 210, 210-1, 210-2, 212, 214, 216, 218a-b, 220, 222, 226, 228, 228-1, 228-2, 228-3, 228-4, 230, 232, 232-1, 232-2, 232-3, 234a-b, 236, 238, 240, 240-1, 240-2, 242, 242-1, 242-2, 242-3, 244, 250, 252, 252-1, 252-2, 254a, 256, 258, 260, 262, 270, 272, 272-1, 272-2, 274, 276, 278, 278-1, 280, 282, 282-1, 282-2, 282-3, 284 may be similar in configuration and/or functionality to similarly named and/or numbered components as described herein. In some embodiments, the fluid delivery system 200 (and/or portion and/or component 210, 210-1, 210-2, 212, 214, 216, 218a-b, 220, 222, 226, 228, 228-1, 228-2, 228-3, 228-4, 230, 232, 232-1, 232-2, 232-3, 234a-b, 236, 238, 240, 240-1, 240-2, 242, 242-1, 242-2, 242-3, 244, 250, 252, 252-1, 252-2, 254a, 256, 258, 260, 262, 270, 272, 272-1, 272-2, 274, 276, 278, 278-1, 280, 282, 282-1, 282-2, 282-3, 284 thereof) may be utilized in accordance with the methods 800, 900 of FIG. 8 and/or FIG. 9 herein, and/or portions or combinations thereof.

Turning now to FIG. 3A, FIG. 3B, FIG. 3C, FIG. 3D, FIG. 3E, FIG. 3F, FIG. 3G, and FIG. 3H, right-front perspective, top, bottom, left, right, front, back, and front cross-sectional views of a modular hub 330 according to some embodiments are shown. In some embodiments, the modular hub 330 may comprise a modular component of a fluid delivery system as described herein. The modular hub 330 may comprise, for example, a cylindrical hub body 232 defining a hub bore 332-1 therethrough, the hub bore 332-1 having an inside hub bore diameter 332-2. According to some embodiments, the modular hub 330 may comprise a vial bevel 332-3 disposed at an opening of the hub bore 332-1 and/or may comprise a plurality of locking slots 334a-b disposed in the sides of the hub body 332. In some embodiments, the modular hub 330 may comprise an assembly flange 336 disposed at an opening of the hub bore 332-1 and/or may comprise a plurality of valve slots 338a-b disposed in the sides of the hub body 332.

According to some embodiments, the modular hub 330 may comprise a fluid outlet bore 340 having an interior fluid outlet bore diameter 340-1. In some embodiments, a valve seat 340-2 may be formed or disposed in the hub bore 332-1 and/or between the hub bore 332-1 and the fluid outlet bore 340. In some embodiments, the modular hub 330 may comprise an insert bore 342 having an interior insert bore diameter 342-1 and/or may comprise and/or define an insert bevel 342-2 and/or an insert recess 342-3. According to some embodiments, the insert recess 342-3 may define and/or the insert bore 342 may comprise and/or define an insert seat 344.

Figure 3A:
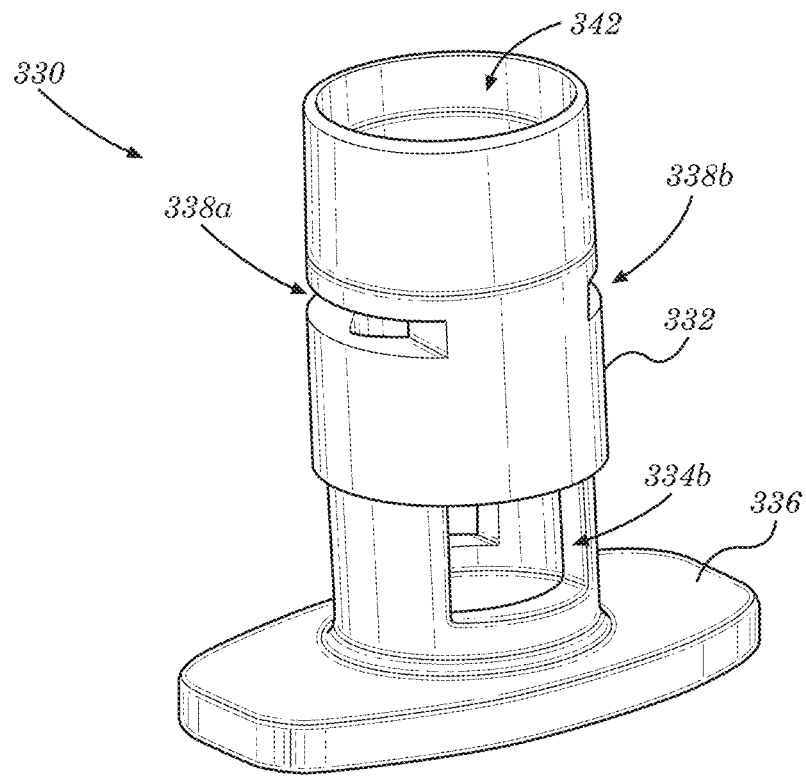
Figure 3B:
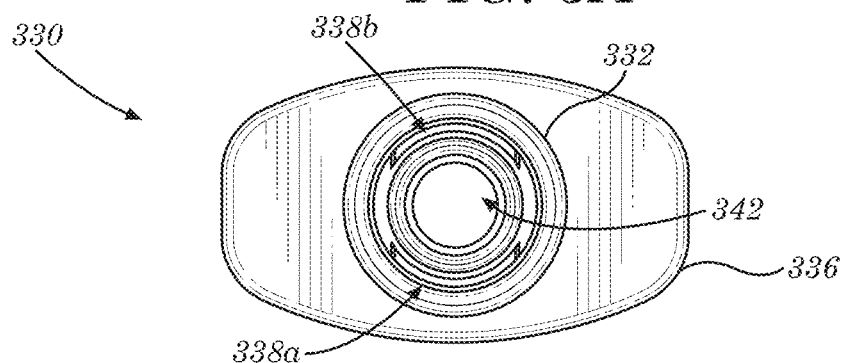
Figure 3C:
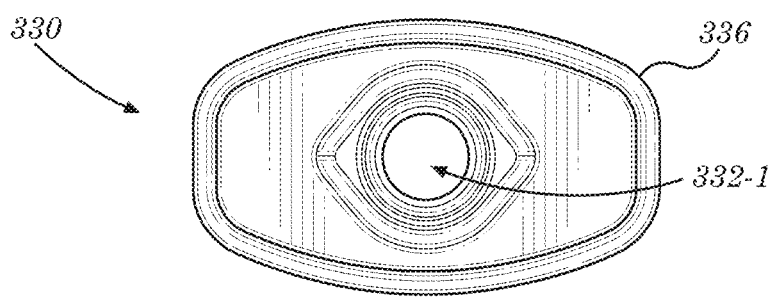
Figure 3D:
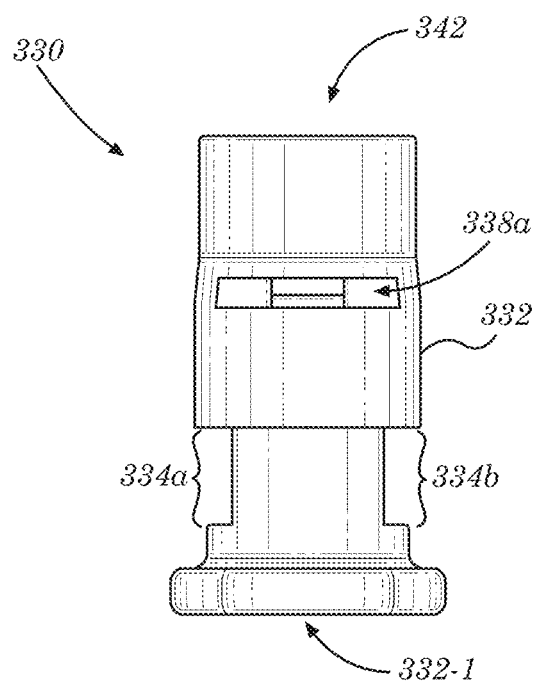
Figure 3E:
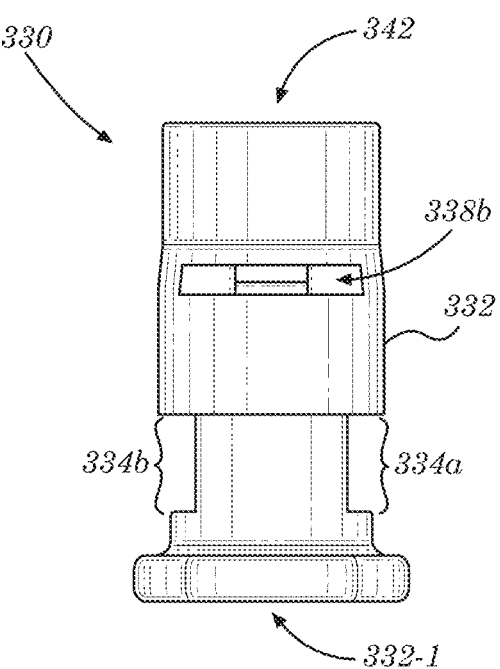
Figure 3F:
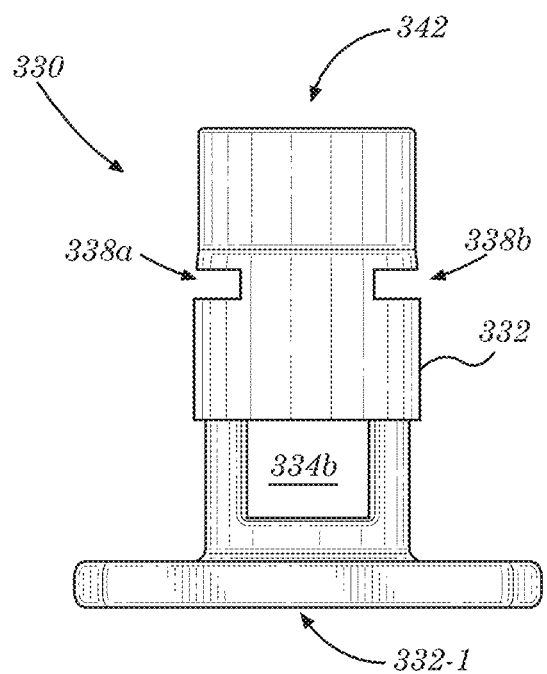
Figure 3G:
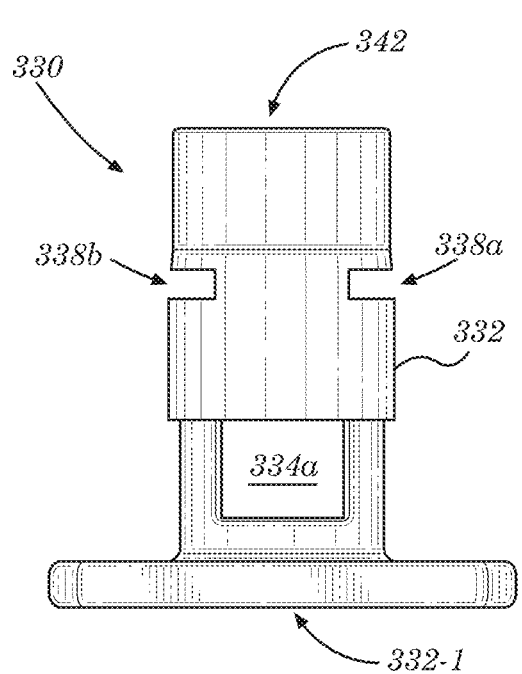
Figure 3H:
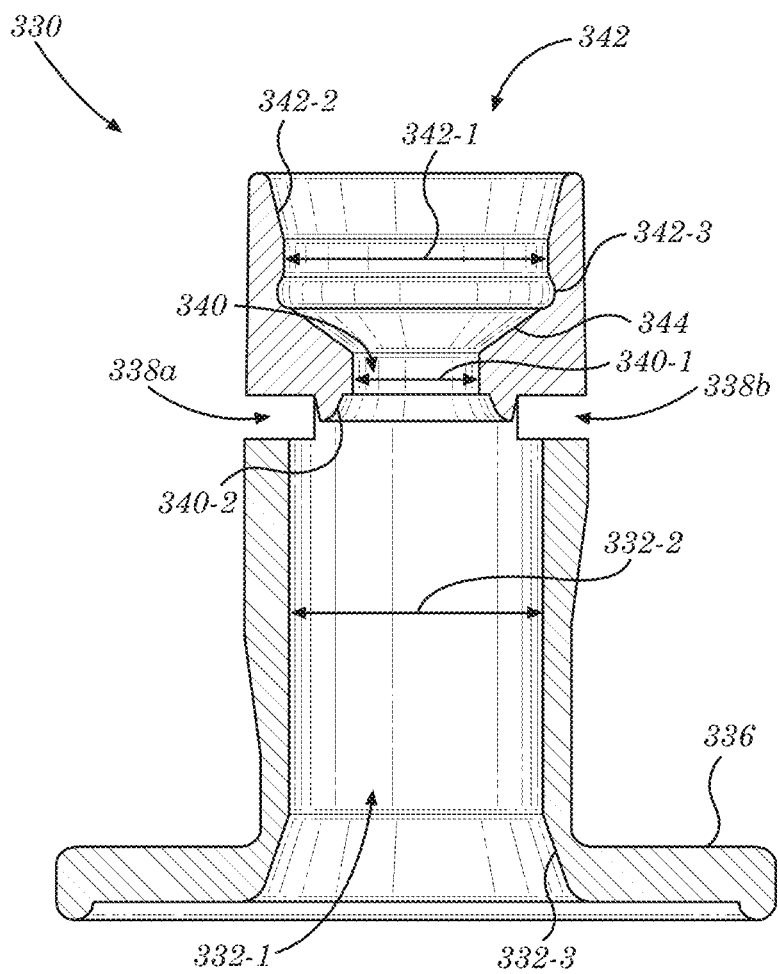

In some embodiments, as best seen in FIG. 3C, the hub bore 332-1 may comprise a non-circular cross-section such as an oval, square, rectangle, triangle, and/or other shape such as an "eye" shape as shown. In such a manner, for example, only BFS vials having similarly-shaped necks (not shown) may be inserted into the hub bore 332-1 and/or may be inserted and seated properly seated to form a water-tight seal therein. According to some embodiments, the hub bore diameter 332-2 may be equal to the insert bore diameter 342-1 and/or the fluid outlet bore diameter 340-1 may be smaller than either or both of the hub bore diameter 332-2 and the insert bore diameter 342-1. In some embodiments, the valve seat 340-2 and/or the insert seat 344 may be shaped to accept a valve and an insert (neither shown), respectively. According to some embodiments, the valve seat 340-2 may be positioned axially adjacent to the valve slots 338a-b such that a portion of a valve inserted into the hub bore 322-1 may seat and/or seal with the valve seat 340-2 while another portion of the valve seats within, protrudes into, and/or is otherwise engaged with each respective valve slot 338a-b. According to some embodiments, the vial bevel 332-3 and the insert bevel 342-2 may be conically-shaped portions that act upon objects inserted axially therein. In the case a pliable and/or compressible object (not shown) having an outside diameter and/or radial extent that exceeds the hub bore diameter 332-2 is urged axially into the hub bore 332-1, for example, the vial bevel 332-3 may provide or exert a radially inward opposing force thereon, causing object to compress, retract, and/or deform—e.g., increasingly as the diameter of the vial bevel 332-3 decreases along the axial insertion path.

According to some embodiments, fewer or more components 332, 332-1, 332-2, 332-3, 334a-b, 336, 338, 340, 340-1, 340-2, 342, 342-1, 342-2, 342-3, 344 and/or various configurations of the depicted components 332, 332-1, 332-2, 332-3, 334a-b, 336, 338, 340, 340-1, 340-2, 342, 342-1, 342-2, 342-3, 344 may be included in the modular hub 330 without deviating from the scope of embodiments described herein. In some embodiments, the components 332, 332-1, 332-2, 332-3, 334a-b, 336, 338, 340, 340-1, 340-2, 342, 342-1, 342-2, 342-3, 344 may be similar in configuration and/or functionality to similarly named and/or numbered components as described herein. In some embodiments, the modular hub 330 (and/or portion and/or component 332, 332-1, 332-2, 332-3, 334a-b, 336, 338, 340, 340-1, 340-2, 342, 342-1, 342-2, 342-3, 344 thereof) may be utilized in accordance with the methods 800, 900 of FIG. 8 and/or FIG. 9 herein, and/or portions or combinations thereof.

Turning now to FIG. 4A, FIG. 4B, FIG. 4C, FIG. 4D, FIG. 4E, FIG. 4F, FIG. 4G, and FIG. 4H, right-front perspective, top, bottom, left, right, front, back, and front cross-sectional views of a modular valve 450 according to some embodiments are shown. In some embodiments, the modular valve 450 may comprise a modular component of a fluid delivery system as described herein. The modular valve 450 may comprise, for example, a cylindrical and/or annular-shaped valve body 452 defining a valve channel 452-1 therethrough, having a valve flap 452-2 disposed therein, and/or one or more mounting wings 454a-b protruding radially from the valve body 452. According to some embodiments, the modular valve 450 may comprise a cylindrical riser 456 extending axially from the valve body 452 and/or an antegrade void 458 formed at the base of the riser 456. In some embodiments, the modular valve 450 may comprise a vial flange 460 formed and/or disposed on an axial-facing surface of the valve body 452 and/or may comprise a seating surface 462 disposed and/or formed on an opposite axial-facing surface of the valve body 452.

Figure 4A:
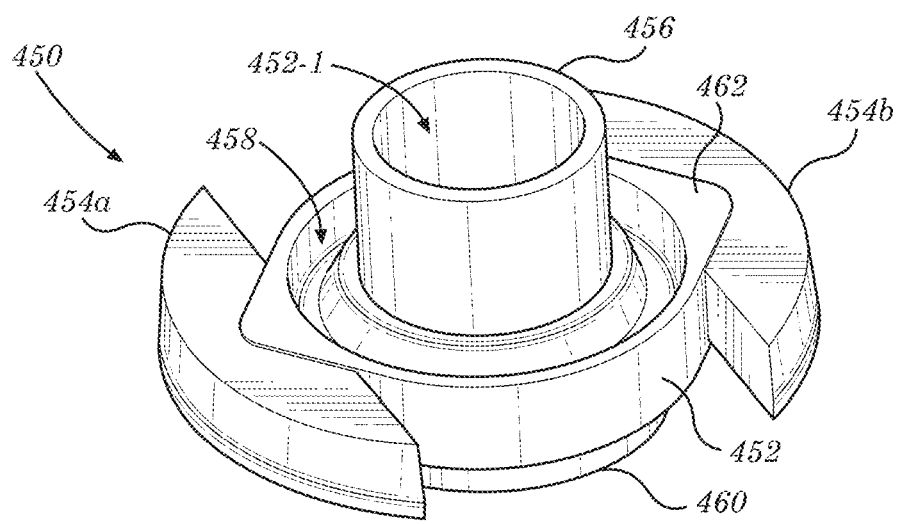
Figure 4B:
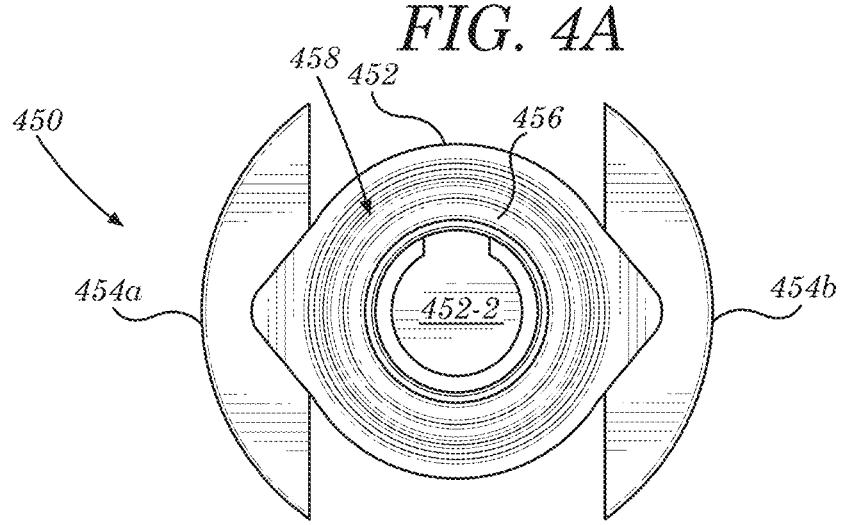
Figure 4C:
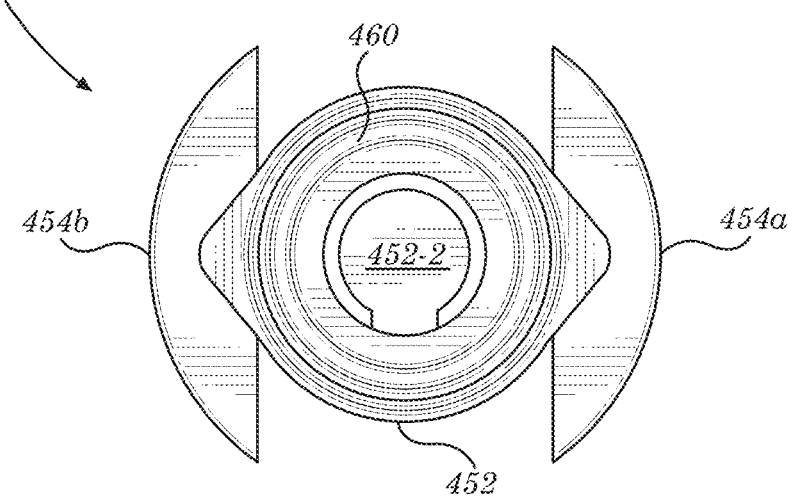
Figures 4D, 4E:
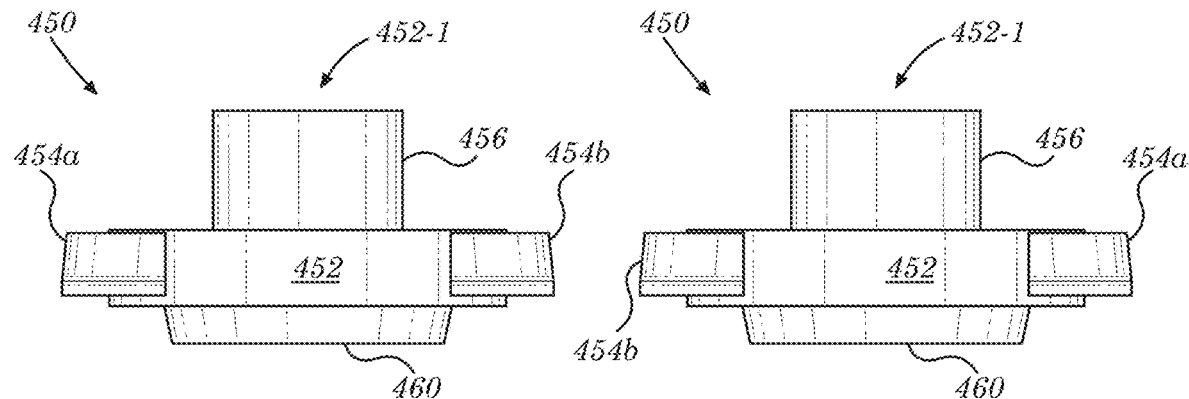
Figures 4F, 4G:
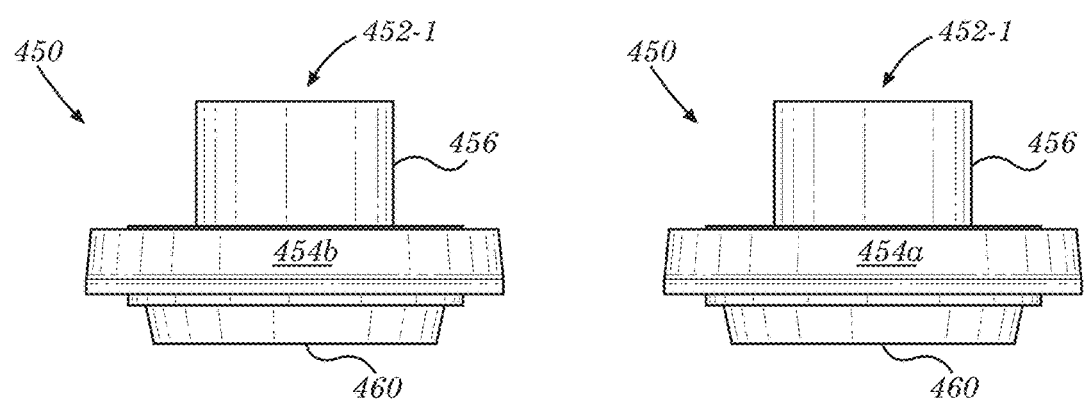
Figure 4H:
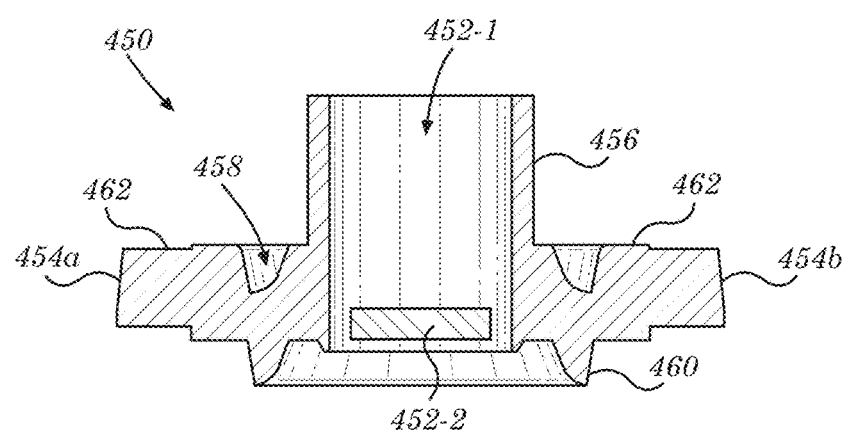
Figure 5A:
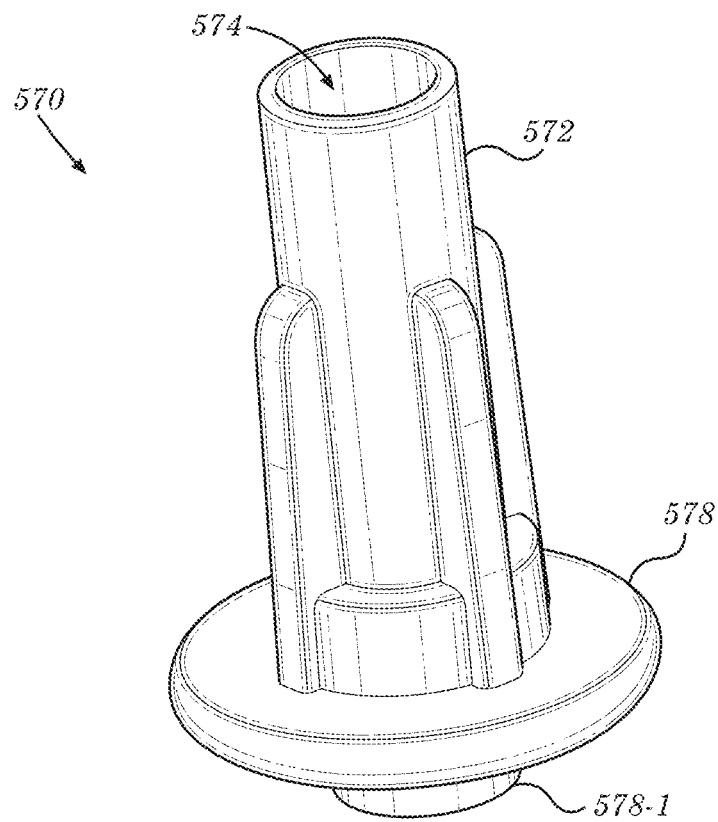
Figure 5B:
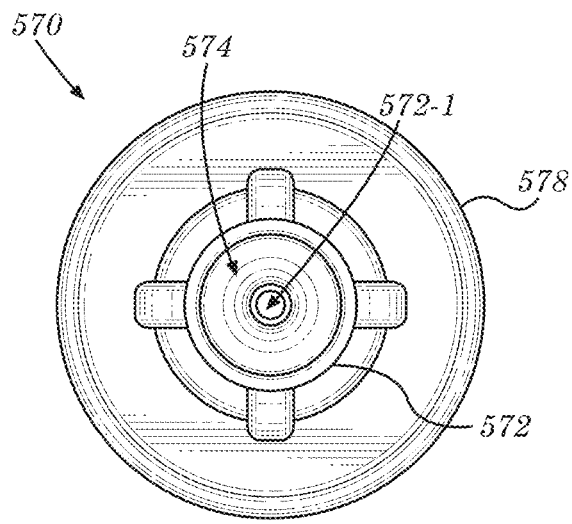
Figure 5C:
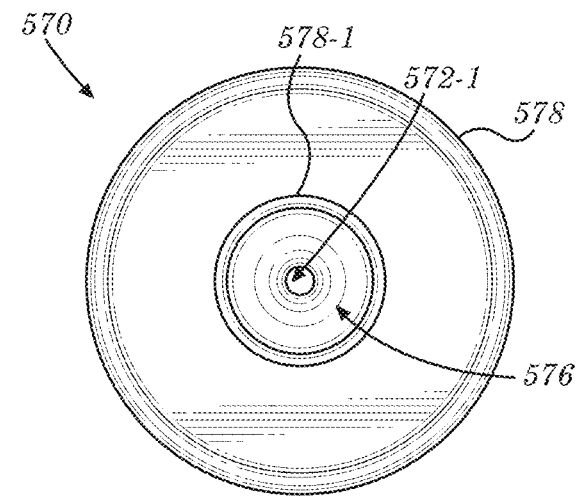
Figure 5D:
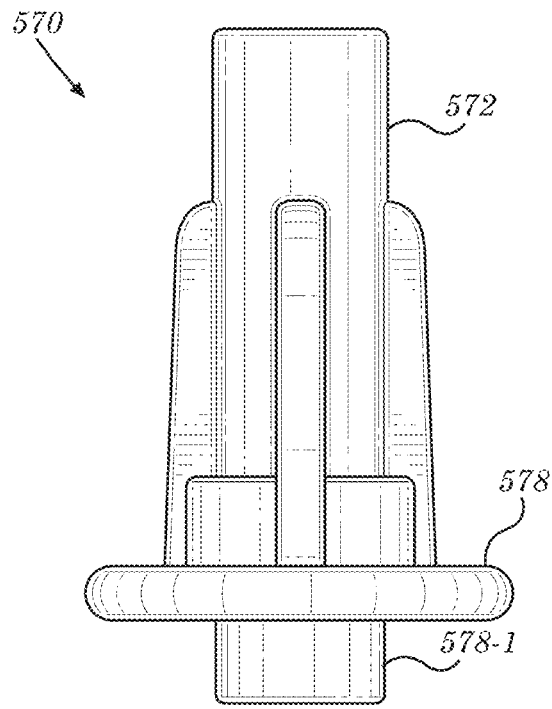
Figure 5E:
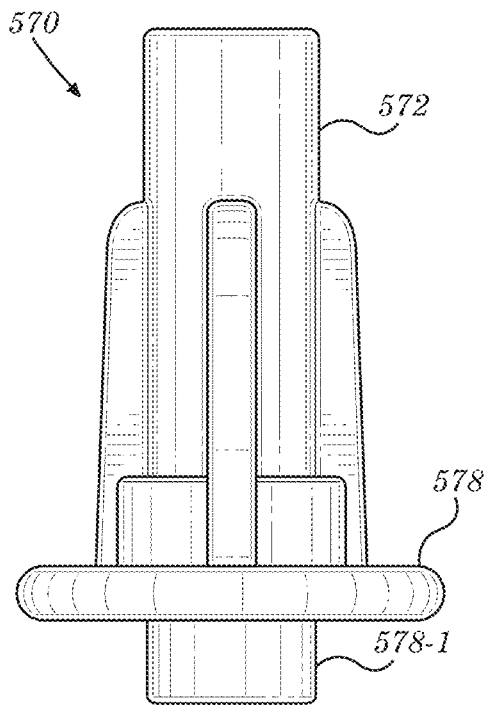
Figure 5F:
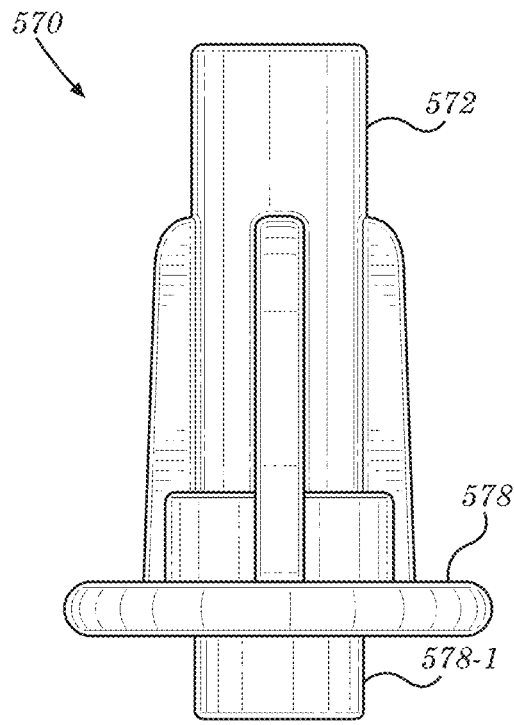
Figure 5G:
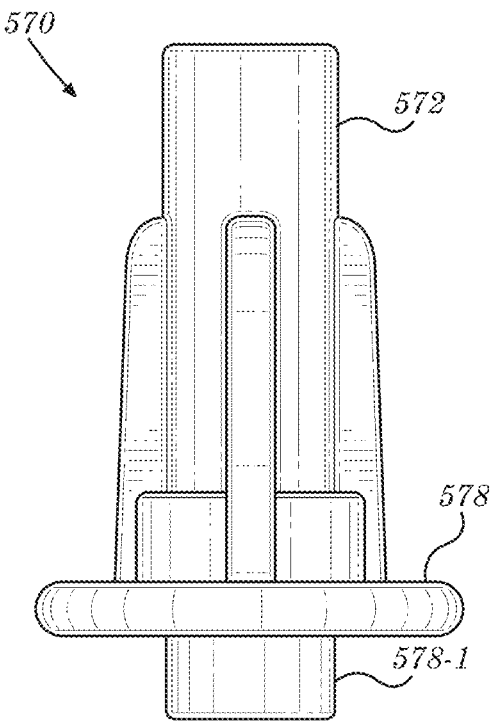
Figure 5H:
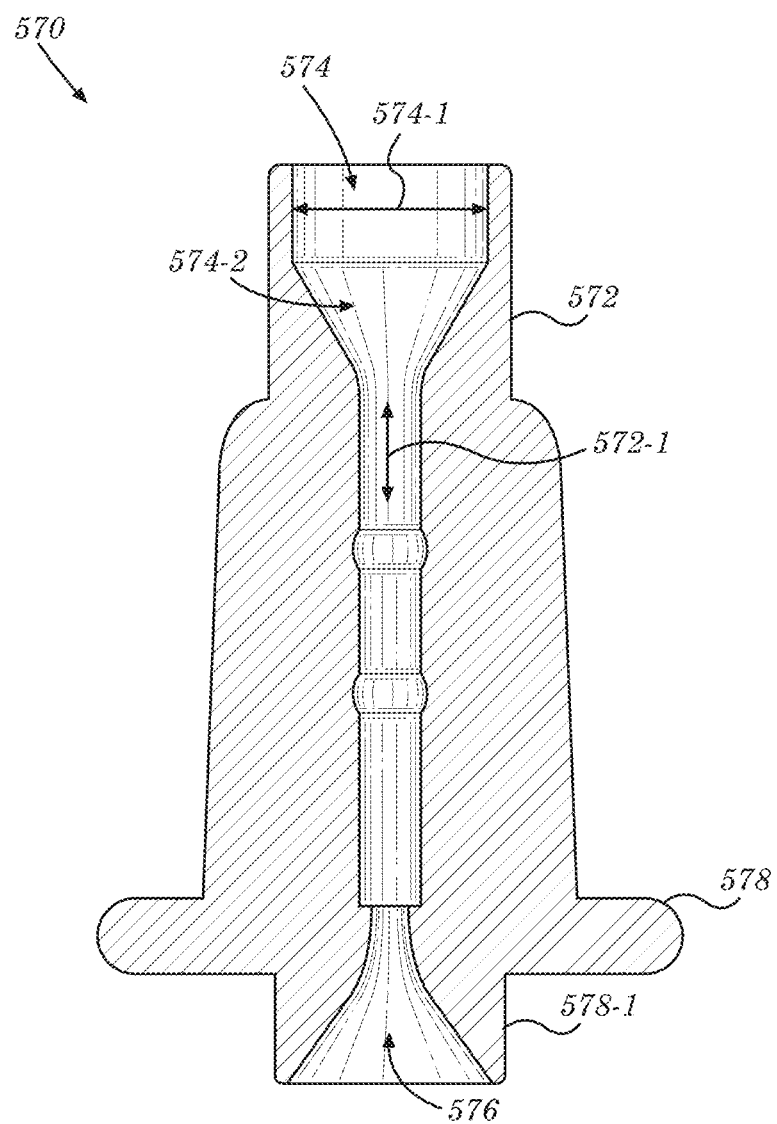
Figure 6A:
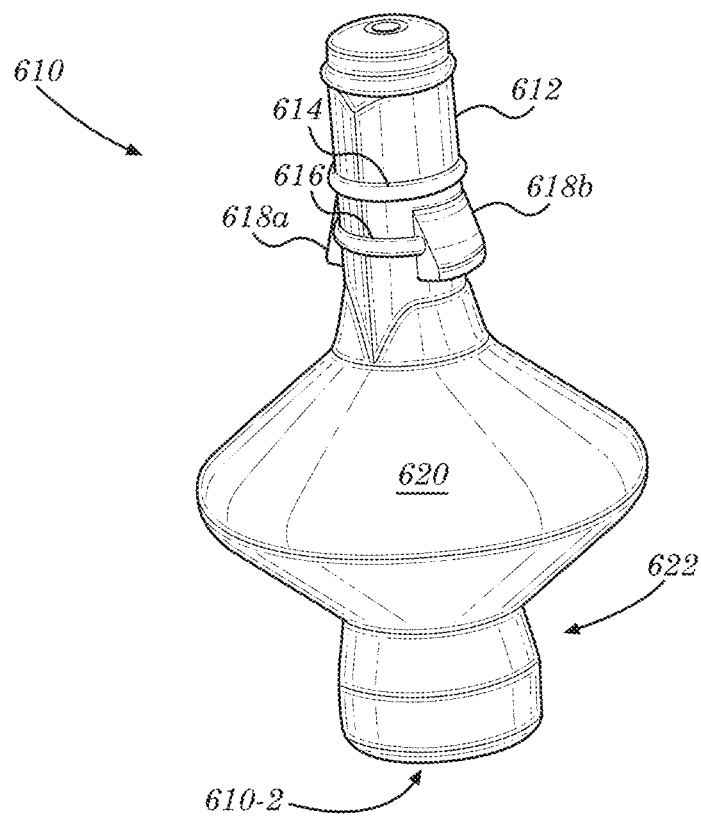
Figure 6B:
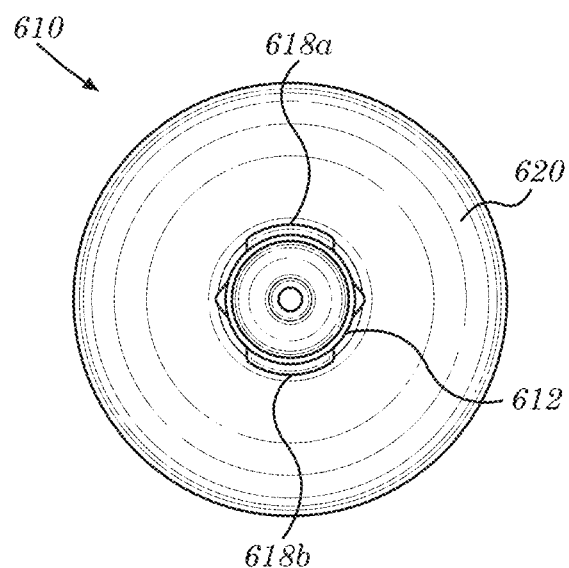
Figure 6C:
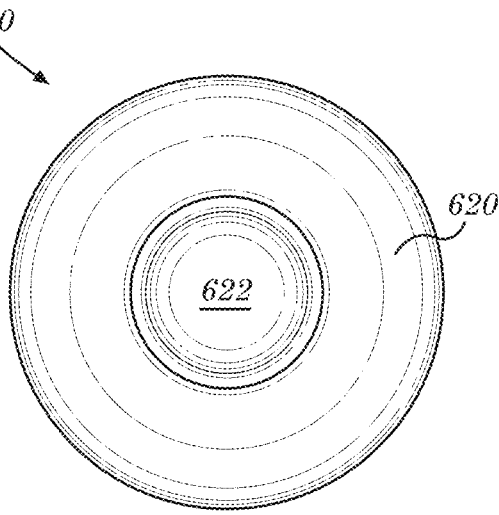
Figure 6D:
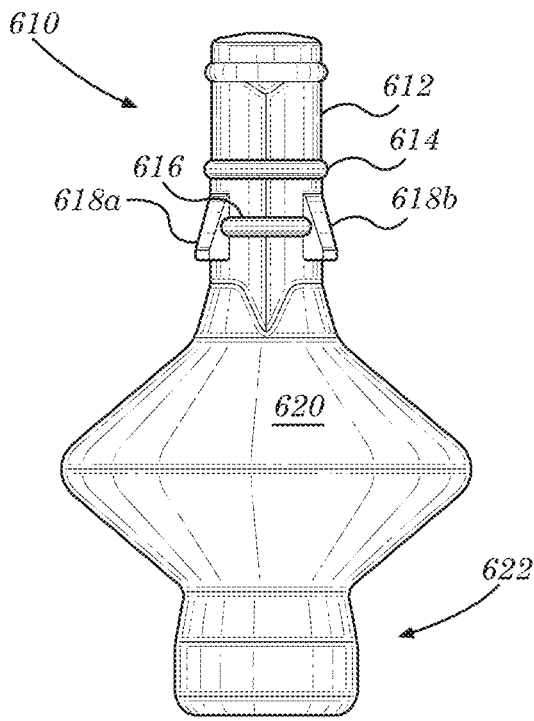
Figure 6E:
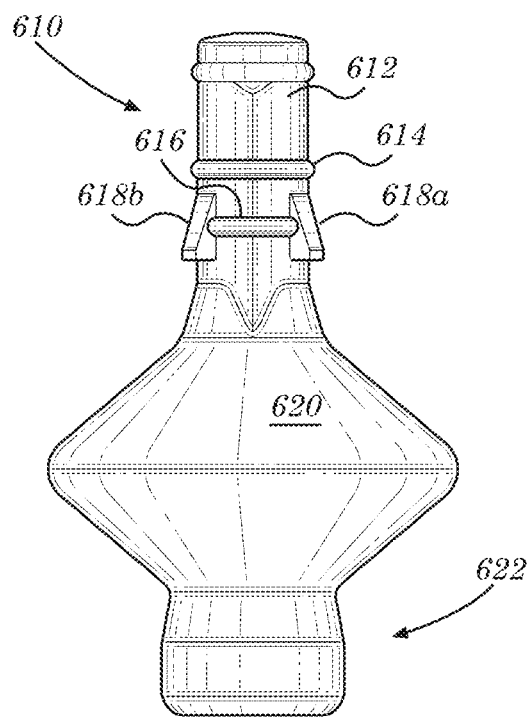
Figure 6F:
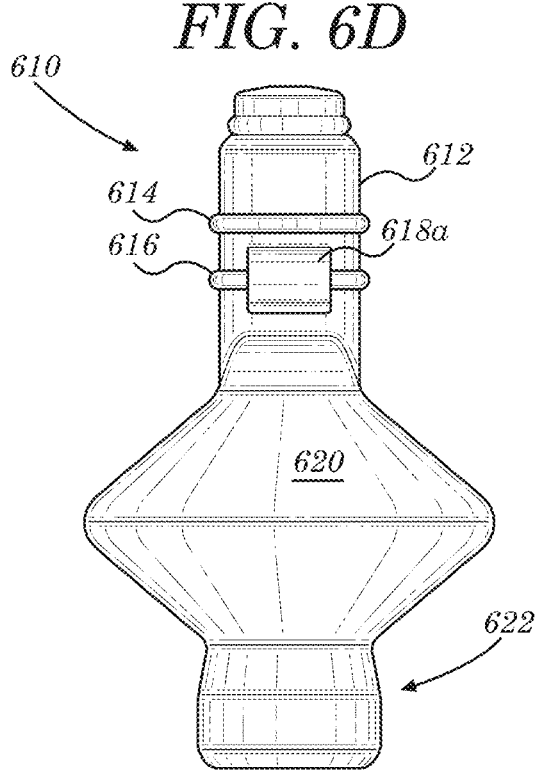
Figure 6G:
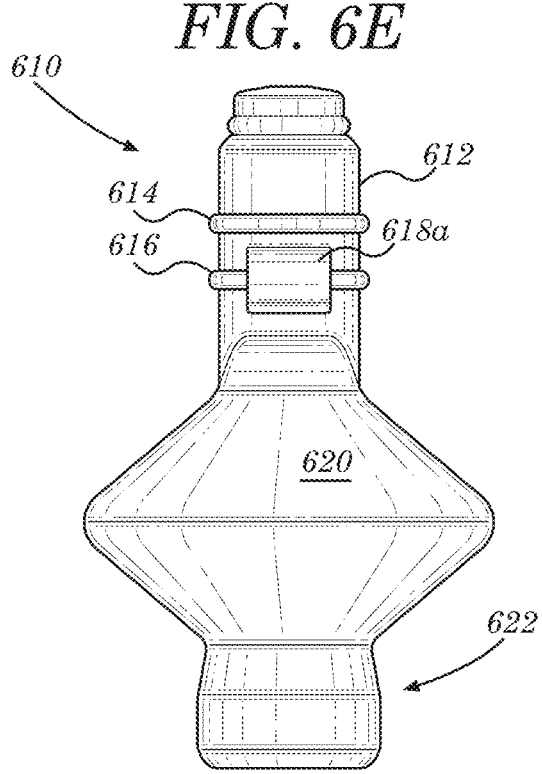
Figure 7A:
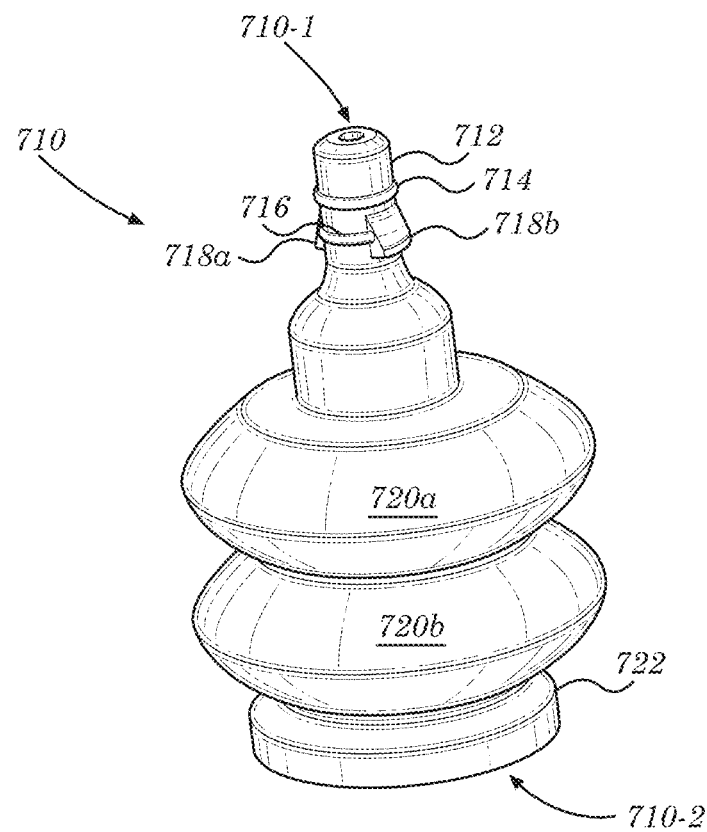
Figure 7B:
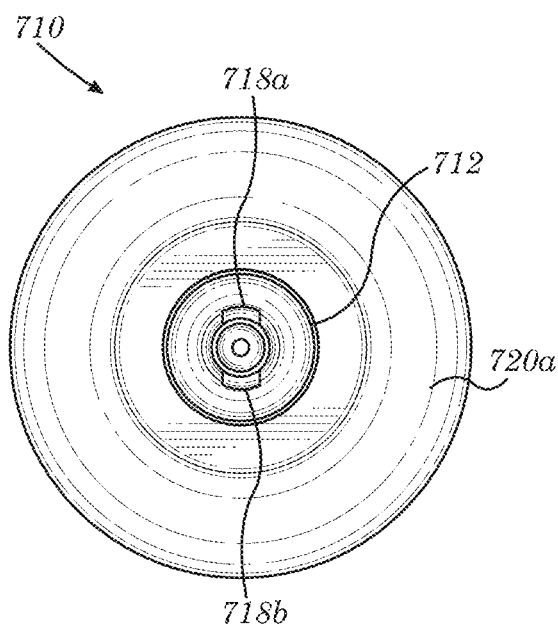
Figure 7C:
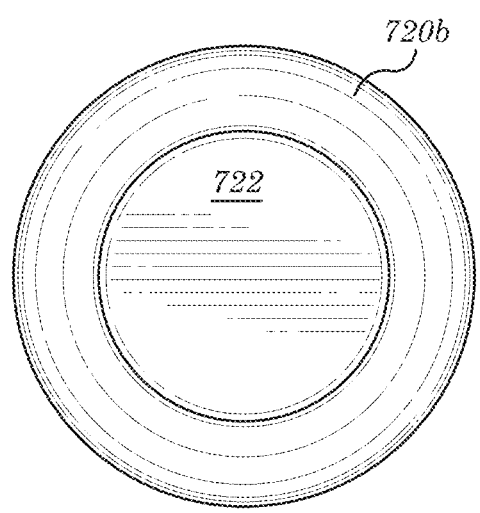
Figure 7D:
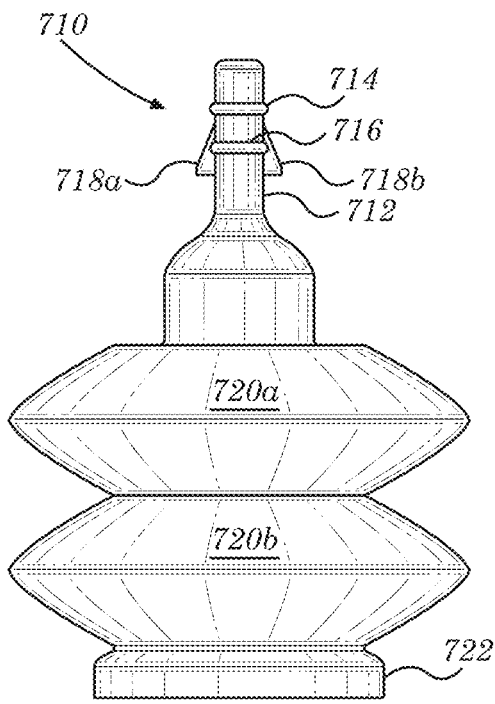
Figure 7E:
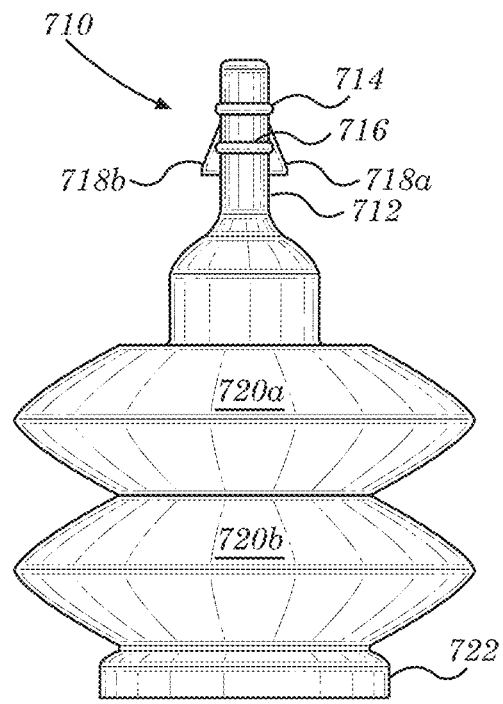
Figure 7F:
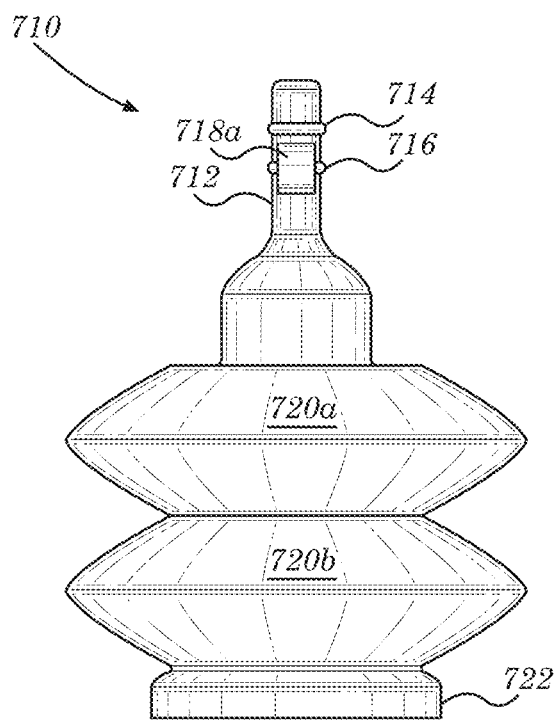
Figure 7G:
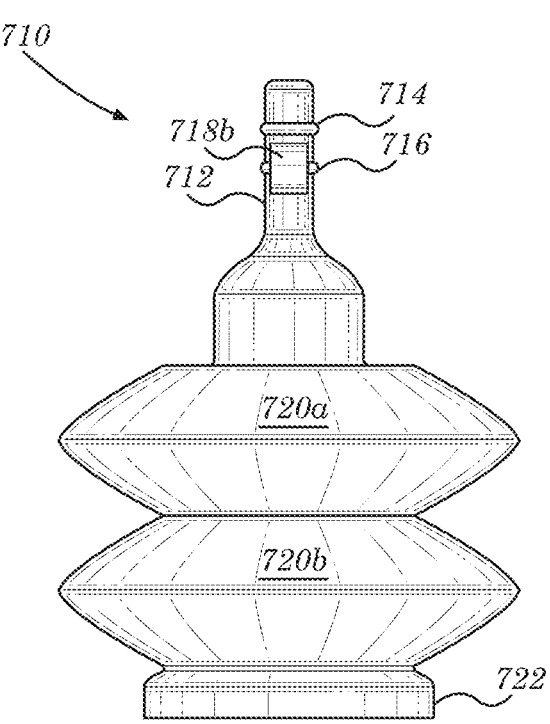

According to some embodiments, the valve body 452 may be shaped to fit within a bore of a modular hub member (not shown). The valve body 452 may be substantially cylindrically or circularly-shaped, for example, or may be "eye" or "almond"-shaped, as depicted in FIG. 4A, FIG. 4B, and FIG. 4C. In some embodiments, the valve flap 452-2 may comprise a portion of pliable material attached along only a portion of a circumference of the interior of the valve channel 452-1 such that it may be selectively and temporarily axially displaced upon application of an axial force thereto. In some embodiments, more rigid rubber or plastic compounds may be utilized to construct the valve flap 452-2 such that larger amounts of axial force are required to bend the valve flap 452-2 and/or such that the valve flap 452-2 may comprise an increased natural spring-effect that urges or biases the valve flap 452-2 to a default or "closed" position, e.g., normal to an axis of the modular valve 450.

In some embodiments, fewer or more components 452, 452-1, 452-2, 454a-b, 456, 458, 460, 462 and/or various configurations of the depicted components 452, 452-1, 452-2, 454a-b, 456, 458, 460, 462 may be included in the modular valve 450 without deviating from the scope of embodiments described herein. In some embodiments, the components 452, 452-1, 452-2, 454a-b, 456, 458, 460, 462 may be similar in configuration and/or functionality to similarly named and/or numbered components as described herein. In some embodiments, the modular valve 450 (and/or portion and/or component 452, 452-1, 452-2, 454a-b, 456, 458, 460, 462 thereof) may be utilized in accordance with the methods 800, 900 of FIG. 8 and/or FIG. 9 herein, and/or portions or combinations thereof.

Turning now to FIG. 5A, FIG. 5B, FIG. 5C, FIG. 5D, FIG. 5E, FIG. 5F, FIG. 5G, and FIG. 5H, right-front perspective, top, bottom, left, right, front, back, and front cross-sectional views of a modular insert 570 according to some embodiments are shown. In some embodiments, the modular insert 570 may comprise a modular component of a fluid delivery system as described herein. The modular insert 570 may comprise, for example, a cylindrical-shaped insert body 572 defining a fluid channel 572-1 therethrough, having an outlet funnel 574 and/or an inlet funnel 576 disposed at opposing ends thereof. According to some embodiments, the outlet funnel 574 may comprise an inside diameter 574-1 configured for various desired fluid delivery applications as described herein (e.g., for acceptance of different gauge needles, nozzles, and/or other delivery methods or applications). In some embodiments, the modular insert 570 may comprise a seating flange 578 and/or a seating flange collar 578-1. As depicted, the seating flange collar 578-1 may house and/or define the inlet funnel 576. According to some embodiments, the seating flange 578 may be rounded at the radial extents thereof, such as to facilitate insertion of the seating flange 578 into a bore (not shown) with a smaller diameter than that of the seating flange 578.

In some embodiments, fewer or more components 572, 572-1, 572-2, 574, 574-1, 576, 578, 578-1 and/or various configurations of the depicted components 572, 572-1, 572-2, 574, 574-1, 576, 578, 578-1 may be included in the modular insert 570 without deviating from the scope of embodiments described herein. In some embodiments, the components 572, 572-1, 572-2, 574, 574-1, 576, 578, 578-1 may be similar in configuration and/or functionality to similarly named and/or numbered components as described herein. In some embodiments, the modular insert 570 (and/or portion and/or component 572, 572-1, 572-2, 574, 574-1, 576, 578, 578-1 thereof) may be utilized in accordance with the methods 800, 900 of FIG. 8 and/or FIG. 9 herein, and/or portions or combinations thereof.

Turning now to FIG. 6A, FIG. 6B, FIG. 6C, FIG. 6D, FIG. 6E, FIG. 6F, and FIG. 6G, right-front perspective, top, bottom, left, right, front, and views of a modular BFS vial 610 according to some embodiments are shown. The BFS vial 610 may, for example, comprise a generally flask-shaped element comprising a bottom 610-2 at one end and comprising a neck 612, a distal or first flange 614, a proximate or second flange 616, and/or a plurality of indexing or coupling elements 618a-b at an opposite end thereof. The first flange 614, second flange 616, and/or coupling elements 618a-b may, in some embodiments, be operable to mate and/or couple with a hub assembly for fluid delivery (not shown), as described herein. In some embodiments, the modular BFS vial 610 may comprise a flask-shaped fluid reservoir 620 disposed between the bottom 610-2 and the neck 612, and/or a compression foot 622 disposed adjacent to and/or at the bottom 610-2.

According to some embodiments, the flask-shaped fluid reservoir 620 may be axially compressed and/or collapsed to expel any fluid stored therein, such as by application of an axial force urging the compression foot 622 toward the neck 612. In some embodiments, the flask-shaped fluid reservoir 620 may be advantageously ergonomic by lending itself to easy operation by a user (not shown) by the user placing two (2) or more fingers (not shown) over the top of the flask-shaped fluid reservoir 620 with their thumb (also not shown) disposed beneath the compression foot 622 at the bottom 610-2. A squeezing motion compressing the fingers toward the thumb may then, in some embodiments, compress and/or deform the flask-shaped fluid reservoir 620 such that it achieves a substantially disk-shaped collapsed appearance and accordingly reduces the volume of the flask-shaped fluid reservoir 620 to substantially zero by expelling substantially all fluid previously stored therein.

In some embodiments, fewer or more components 610-2, 612, 614, 616, 618a-b, 620, 622 and/or various configurations of the depicted components 610-2, 612, 614, 616, 618a-b, 620, 622 may be included in the modular BFS vial 610 without deviating from the scope of embodiments described herein. In some embodiments, the components 610-2, 612, 614, 616, 618a-b, 620, 622 may be similar in configuration and/or functionality to similarly named and/or numbered components as described herein. In some embodiments, the modular BFS vial 610 (and/or portion and/or component 610-2, 612, 614, 616, 618a-b, 620, 622 thereof) may be utilized in accordance with the methods 800, 900 of FIG. 8 and/or FIG. 9 herein, and/or portions or combinations thereof.

Turning now to FIG. 7A, FIG. 7B, FIG. 7C, FIG. 7D, FIG. 7E, FIG. 7F, and FIG. 7G, right-front perspective, top, bottom, left, right, front, and views of a modular BFS vial 710 according to some embodiments are shown. The BFS vial 710 may, for example, comprise an accordion or "concertina"-shaped element comprising a top or outlet 710-1 and a bottom 710-2. In some embodiments, the BFS vial 710 may comprise (e.g., at or adjacent to the outlet 710-1) a neck 712, a distal or first flange 714, a proximate or second flange 716, and/or a plurality of indexing or coupling elements 718a-b. The first flange 714, second flange 716, and/or coupling elements 718a-b may, in some embodiments, be operable to mate and/or couple with a hub assembly for fluid delivery (not shown), as described herein. In some embodiments, the modular BFS vial 710 may comprise a "concertina"-shaped fluid reservoir 720a-b disposed between the top 710-1 and the bottom 710-2, and/or a compression foot 722 disposed adjacent to and/or at the bottom 710-2. In some embodiments, the "concertina"-shaped fluid reservoir 720a-b may comprise and/or define a plurality of segments, volumes, and/or lobes such as an upper or first lobe 720a and a lower or second lobe 720b formed and/or joined therebetween. Fewer or more lobes 720a-b may be utilized in some embodiments.

According to some embodiments, the lobes 720a-b may be axially compressed and/or collapsed to expel any fluid stored therein, such as by application of an axial force urging the compression foot 722 toward the neck 712 and/or the top 710-1. In some embodiments, the lobes 720a-b may be advantageously ergonomic by lending themselves to easy operation by a user (not shown) by the user placing two (2) or more fingers (not shown) over the top of the first lobe 720a with their thumb (also not shown) disposed beneath the compression foot 722 at the bottom 710-2. A squeezing motion compressing the fingers toward the thumb may then, in some embodiments, compress and/or deform each of the lobes 720a-b such that they each achieve a substantially disk-shaped collapsed appearance and accordingly reduce the volume of the "concertina"-shaped fluid reservoir 720a-b to substantially zero by expelling substantially all fluid previously stored therein.

In some embodiments, fewer or more components 710-1, 710-2, 712, 714, 716, 718a-b, 720a-b, 722 and/or various configurations of the depicted components 710-1, 710-2, 712, 714, 716, 718a-b, 720a-b, 722 may be included in the modular BFS vial 710 without deviating from the scope of embodiments described herein. In some embodiments, the components 710-1, 710-2, 712, 714, 716, 718a-b, 720a-b, 722 may be similar in configuration and/or functionality to similarly named and/or numbered components as described herein. In some embodiments, the modular BFS vial 710

(and/or portion and/or component 710-1, 710-2, 712, 714, 716, 718*a-b*, 720*a-b*, 722 thereof) may be utilized in accordance with the methods 800, 900 of FIG. 8 and/or FIG. 9 herein, and/or portions or combinations thereof.

III. Fluid Delivery Methods

FIG. 8 is a perspective flow diagram of a method 800 according to some embodiments. The method 800 may, for example, illustrate an exemplary use of the various fluid delivery systems and/or components thereof, as described herein. The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure.

In some embodiments, as shown in FIG. 8, the delivery system may be delivered with a pack of BFS vials 802 and a corresponding number of fully assembled delivery assemblies 826 (e.g., with safety covers 828), at 801. A user may then, according to some embodiments, simply tear away one of the vials 810 from the pack 802 when ready to deliver the single dose of fluid agent, at 803. In some embodiments, the user may then attach the removed vial 810 to one of the delivery assemblies 826 by pressing (e.g., axially) them together, e.g., until the vial 810 snaps, clicks, and/or locks into place in the delivery assembly 826, at 805. According to some embodiments, the user may then remove the safety cover 828 from the combined vial 810 and delivery assembly 826, thereby exposing the needle 880 (or other appropriate administration member), at 807. In some embodiments, the user may then administer the fluid agent (either self-administration or administration to another person), at 809. Once finished, the safety cover 828 may be placed back on to the delivery assembly 826 and the contents can be discarded in the appropriate biohazard waste receptacle, at 811.

The delivery assembly 826 is generally configured to allow delivery of the agent to the patient in a relatively simple manner, without requiring specialized training for administering the agent. In some embodiments, the delivery assembly 828 is designed such that a person administering the fluid agent (e.g., administrator), which could also include self-administration, need only position the device upon the administration site (e.g., shoulder, arm, chest, nose, ear, eye, etc.), and then fully compress the BFS vial 810 (and/or a fluid reservoir thereof) containing the dose of fluid agent, thereby delivering the correct predefined dosage to the patient. The delivery assembly 826 may be further configured such that, in the event that a needle 880 is required (i.e., because the delivery method is an injection), needle penetration is limited to the correct length and orientation within the administration site. For example, in some embodiments, the needle 880 is positioned substantially perpendicular relative to a plane along which the distal end of the insert lies, such that the needle 880 is configured to be inserted into a patient's skin at a substantially perpendicular angle and the distal end of the insert is configured to contact the patient's skin indicating adequate depth of penetrating for injection of the fluid agent.

Accordingly, the delivery assembly 826 may not require a trained, skilled healthcare profession for administration of vaccines or drugs. As such, the delivery assembly 826 may be particularly useful in situations in which vaccines or drugs are being administered in non-healthcare related facilities (e.g., outside of clinics or hospitals) and given to large numbers of individuals over a short period of time by a non-professional.

Referring now to FIG. 9, a flow diagram of a method 900 according to some embodiments is shown. The method 900 may comprise, for example, separating a BFS vial from a BFS manifold, at 902. A user may grab an individual vial and twist or bend it to separate it from the BFS manifold at one or more preconfigured breakage or junction points, for example. According to some embodiments, the method 900 may comprise coupling the BFS vial to a delivery hub, at 904. The coupling may comprise, for example, applying axial force (e.g., via a grip plate of the BFS vial and an assembly flange of the assembly hub) that urges a BFS vial axially into a bore of a modular assembly hub (e.g., as described herein), e.g., until engagement elements integral to the BFS vial click or snap into appropriately indexed retention features of the assembly hub. In some embodiments, the method 900 may comprise removing a safety cap, at 906. Axial force may be applied to separate the cap from the assembly hub, for example, exposing an administration member such as a needle, nozzle, dropper, or the like. According to some embodiments, the method 900 may comprise administering a dose of fluid, at 908. The administration element of the assembly hub may be engaged with a patient, for example, and a collapsible and integral reservoir of the BFS vial may be squeezed (e.g., via application of inward radial force) to force fluid therefrom. According to some embodiments, the fluid may be forced in an antegrade axial direction such that it displaces a valve flap of a one-way valve, thereby allowing the fluid to proceed axially into the administration element and be delivered to the patient. In some embodiments, the method 900 may comprise replacing the safety cap, at 910. According to some embodiments, the method 900 may comprise disposing of the delivery system, at 912. In such a manner, for example, a low-cost, easily transported and more easily stored fluid delivery system may be provided that allows unskilled users to administer and/or self-administer.

IV. Additional Embodiments

FIG. 10 shows perspective views of modular delivery or hub assemblies 1026*a-d* configured for different methods of delivery (e.g., intramuscular, subcutaneous, intravenous, and intradermal injection). In some embodiments, each modular hub assembly 1026*a-d* may comprise a respective modular hub element 1030*a-d*, a modular valve element 1050*a-d*, a modular insert element 1070*a-d*, and/or a modular needle (or other administration) element 1080*a-d*. As depicted in FIG. 10, the various respective needle elements 1080*a-d* may be configured for different delivery/administration requirements. For example, the needle elements 1080*a-d* may have varying lengths in the range of about one and one half millimeters (1.5 mm) to twenty-five millimeters (25 mm)—e.g., with a first needle element 1080*a* being the longest, a second needle elements 1080*b* being shorter than the first needle element 1080*a*, a third needle elements 1080*c* being shorter than the second needle element 1080*b*, and/or a fourth needle elements 1080*d* being shorter than the third needle element 1080*c*. According to some embodiments, lengths of the needle elements 1080*a-d* may be in the range of one half millimeter (0.5 mm) to fifty millimeters (50 mm). In some embodiments, the only structural differences between the various hub assemblies 1026a-d may be the lengths (and/or thicknesses) of the needle elements 1080a-d. Each of the other modular components 1030a-d, 1050a-d, 1070a-d may, for example, be identical. Accordingly, the modular construction of the delivery assemblies 1026a-d may allow for rapid manufacturing reconfigurations of one or more components with minimal costs to create new delivery assembly configurations that meet specific needs (i.e., different modes of delivery depending on agent to be delivered, such as subcutaneous, intramuscular, intradermal, intravenous injection, spray, or droplet delivery). For example, the modular hub element 1030a-d and the modular valve element 1050a-d may remain the same construction (dimensions and material), while the modular insert element 1070a-d may be changed to account for different sized needle elements 1080a-d and/or nozzle types, depending on the type of delivery and/or type of fluid agent to be delivered.

V. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/ or" clause, whether related or unrelated to those elements specifically identified, unless clearly indicated to the contrary.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A modular injectable delivery system for injection of a fluid agent from a BFS vial into a patient, the modular injectable delivery system comprising:

an administration member for injecting the fluid agent into the patient, the administration member comprising a needle defining a distal end and a proximate end, the distal end comprising a point for piercing the patient, the administration member being retained by a thermoplastic polymer element, and the thermoplastic polymer element comprising a first molded coupling feature adjacent to the proximate end of the needle; and a fluid delivery hub defining a cylindrical body comprising a first end and a second end, the fluid delivery hub comprising a second molded coupling feature at the second end thereof, defining a bore between the first and second ends, and comprising a recess within the bore proximate to the first end thereof, the bore at the first end being shaped to receive a neck of a BFS vial containing the fluid agent and the recess being shaped to receive a mating feature of the neck of the BFS vial, and the second molded coupling feature being selectively engaged with the first molded coupling feature of the thermoplastic polymer element.

2. The modular injectable delivery system of claim 1, wherein the mating feature of the neck of the BFS vial comprises a rounded exterior flange.

3. The modular injectable delivery system of claim 1, further comprising:
a removable cap selectively coupled to cover the distal end of the needle.

4. The modular injectable delivery system of claim 1, wherein the neck of the BFS vial is cylindrically shaped, in fluid communication with a fluid reservoir containing the fluid agent, and comprises a seal at an end thereof.

5. The modular injectable delivery system of claim 1, further comprising:
the BFS vial.

* * * * *